United States Patent [19]

Yoshikumi et al.

[11] 4,372,948

[45] Feb. 8, 1983

[54] DERIVATIVE OF SACCHARIDE AND PHYSIOLOGICALLY ACTIVE AGENT CONTAINING THE SAME

[75] Inventors: Chikao Yoshikumi, Kunitachi; Fumio Hirose, Tokyo; Yoshio Ohmura, Funabashi; Takayoshi Fujii, Tokyo; Masanori Ikuzawa, Tachikawa; Kenichi Matsunaga, Tokyo; Takao Ando, Tokyo; Minoru Ohhara, Tokyo, all of Japan

[73] Assignee: Kureha Kagaku Kogyo Kabushiki Kaisha, Tokyo, Japan

[21] Appl. No.: 247,521

[22] Filed: Mar. 25, 1981

[30] Foreign Application Priority Data

Apr. 11, 1980 [JP] Japan .................................. 55-47654

[51] Int. Cl.[3] ...................... A61K 31/70; C08B 37/00
[52] U.S. Cl. ...................................... 424/180; 536/53; 536/22
[58] Field of Search ...................... 536/18, 53; 424/180

[56] References Cited

U.S. PATENT DOCUMENTS 2,659,689 11/1953 Schreiber .

FOREIGN PATENT DOCUMENTS 2018135 10/1979 United Kingdom .
2018592 10/1979 United Kingdom .
2022411 12/1979 United Kingdom .
2029698 3/1980 United Kingdom .

OTHER PUBLICATIONS

Yoshiuiki Inoue, "Chemical Abstracts", *Organic Chemistry*, cols. 2001–2003.
Annual Reports in Medicinal Chemistry, vol. 10, (1975), pp. 306–314.

*Primary Examiner*—Alan Siegel
*Attorney, Agent, or Firm*—Wegner & Bretschneider

[57] ABSTRACT

The novel derivatives of saccharide obtained by bringing a saccharide into reaction with an ester of aminobenzoic acid, an aminobenzoic acid amide, an aminophenylacetic acid or an ester thereof have various physiological activities.

36 Claims, 29 Drawing Figures

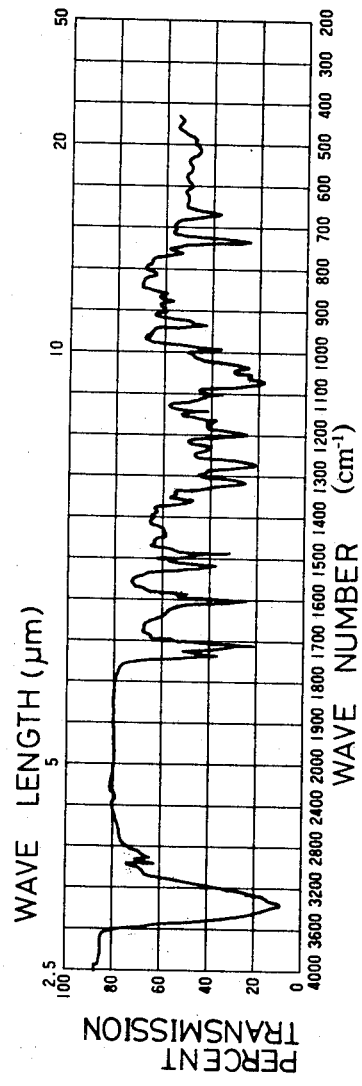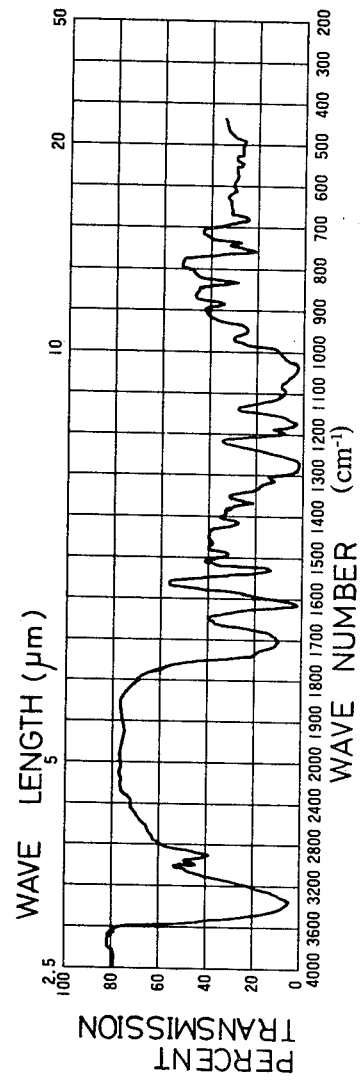

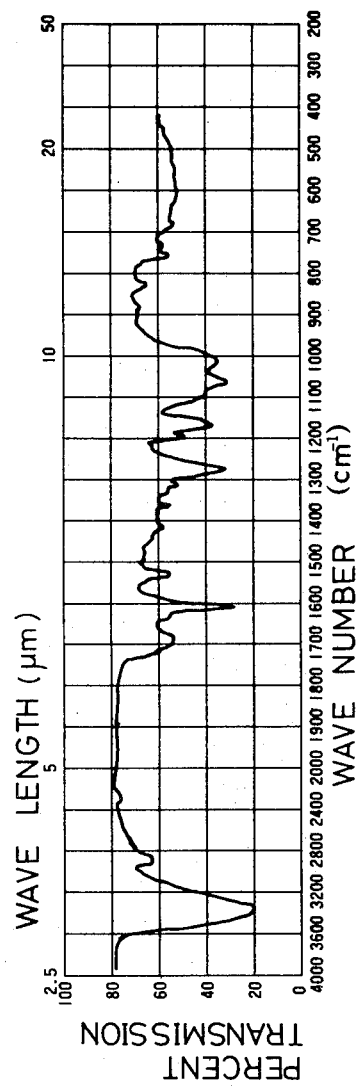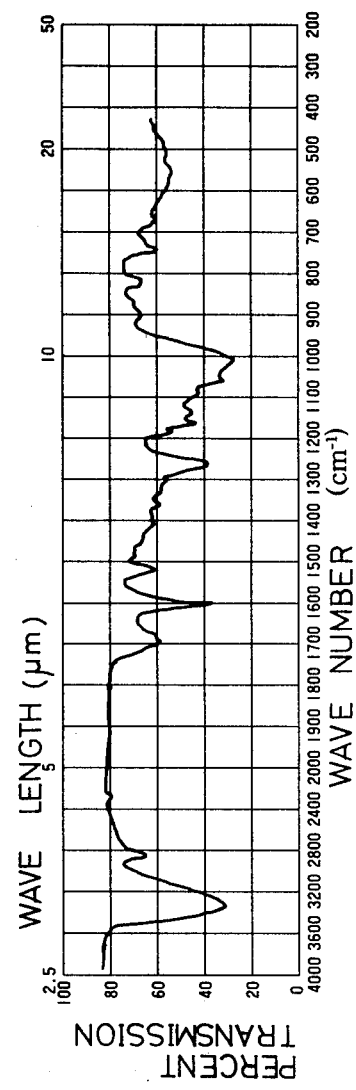

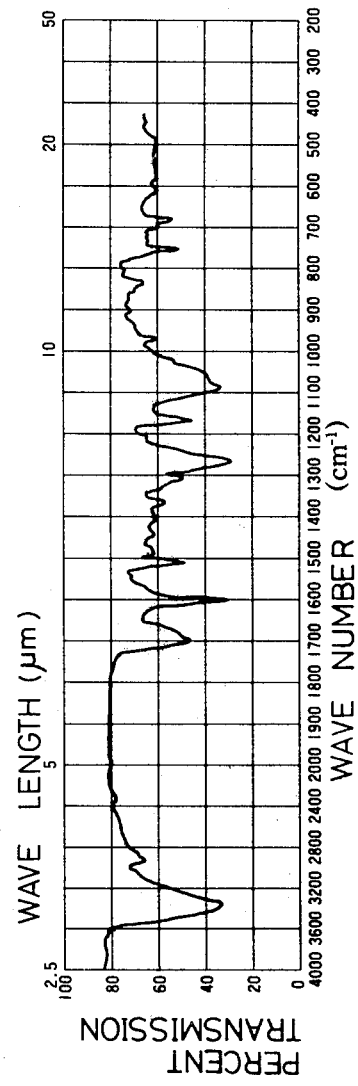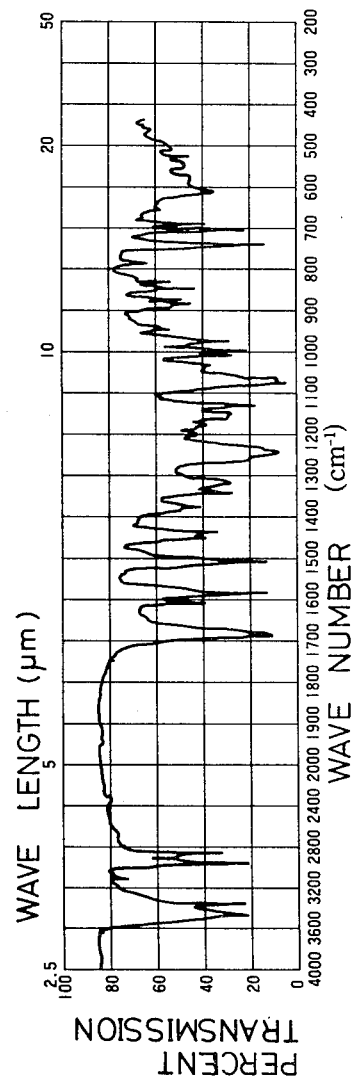

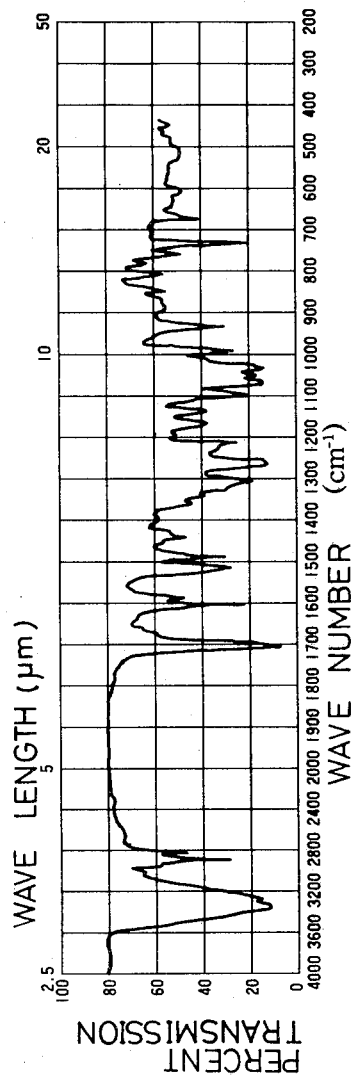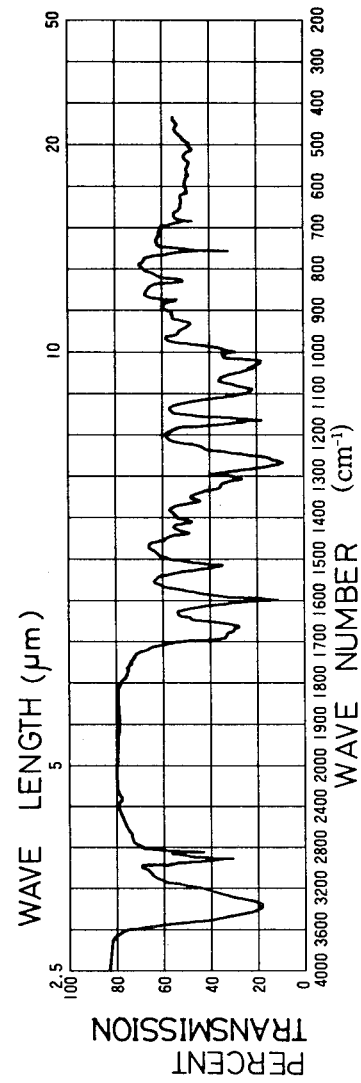

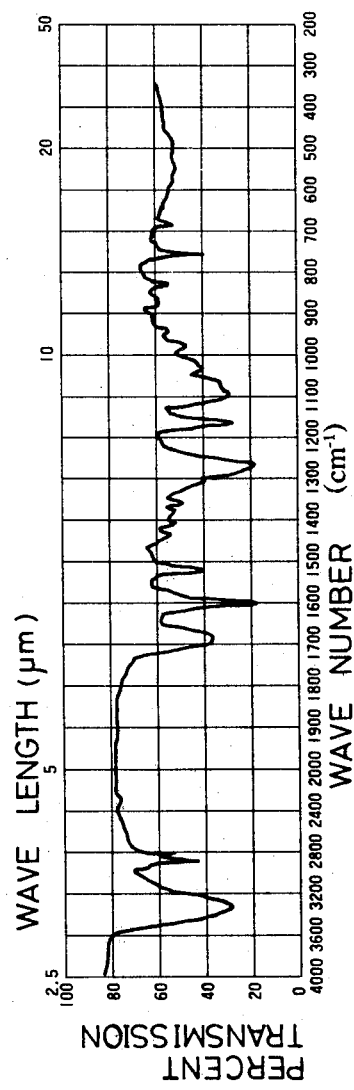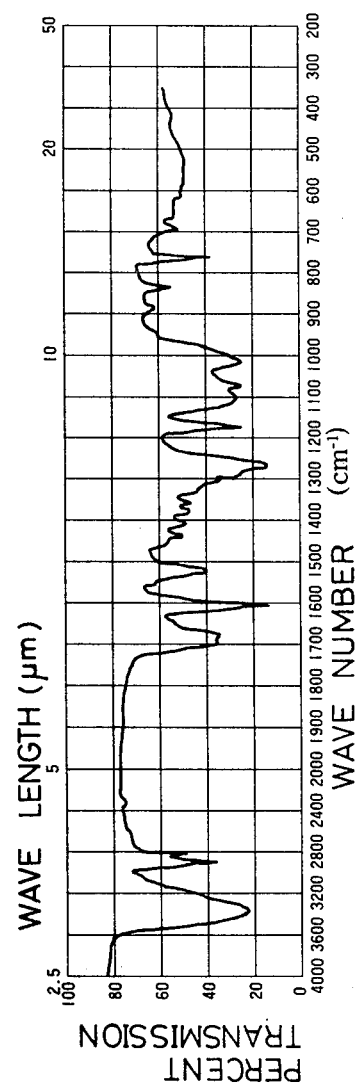

DERIVATIVE OF SACCHARIDE AND PHYSIOLOGICALLY ACTIVE AGENT CONTAINING THE SAME

SUMMARY OF THE INVENTION

The present invention relates to novel derivatives of a saccharide and physiologically active agents having the novel derivatives of a saccharide as an active ingredient thereof.

The novel derivatives of a saccharide according to the present invention are represented by the following general formula (I):

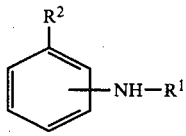

wherein $R^1$ represents a residue of mono-, di- or trisaccharide; $R^2$ represents

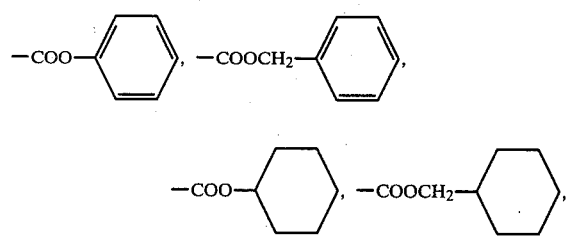

—CONH$_2$ or —CH$_2$COOR$^3$ and $R^3$ represents a hydrogen atom, a lower alkyl group or an equivalent of pharmaceutically acceptable metal.

The novel derivative of a saccharide represented by the formula (I) is useful as a pharmaceutical agent because of its physiological activities of reducing blood sugar level, of reducing blood pressure level, of anti-tumour, of suppressing central nerve and of anti-inflammatory.

BRIEF EXPLANATION OF DRAWINGS

In Drawings, FIGS. 1 to 26 show the respective infrared absorption spectra of the derivatives of a saccharide according to the present invention.

DETAILED DESCRIPTION OF THE INVENTION

Figure 1:
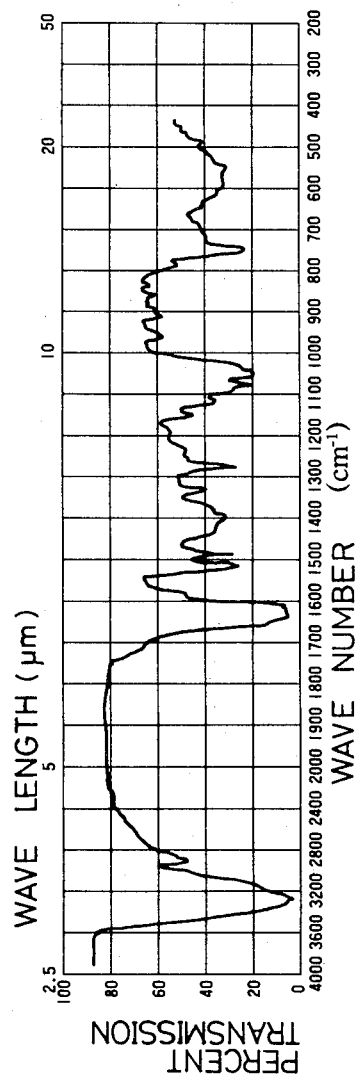
Figure 2:
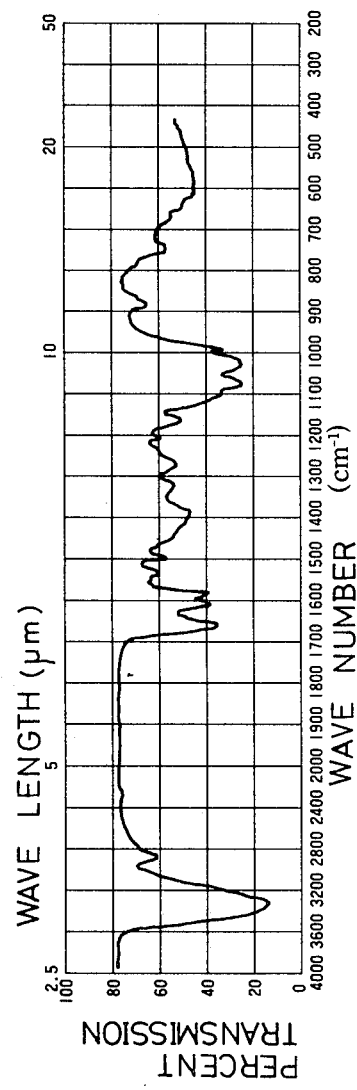
Figure 3:
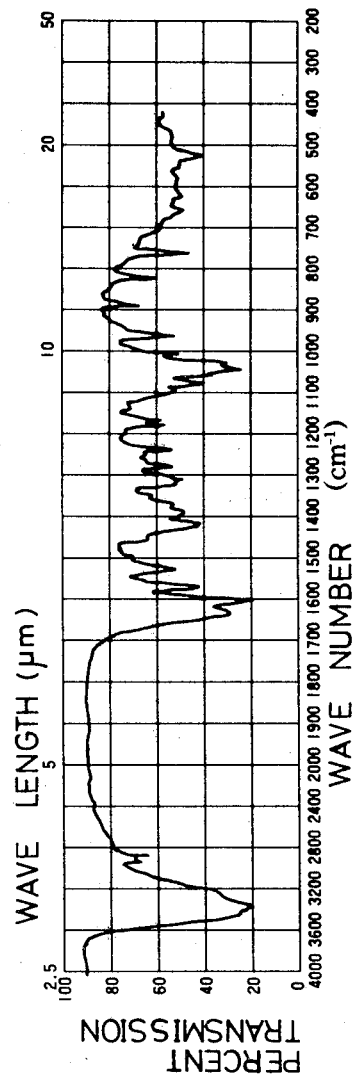
Figure 4:
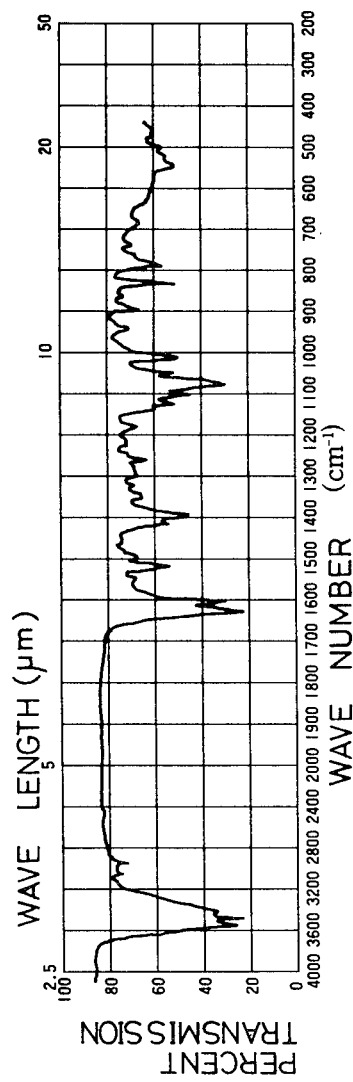
Figure 5:
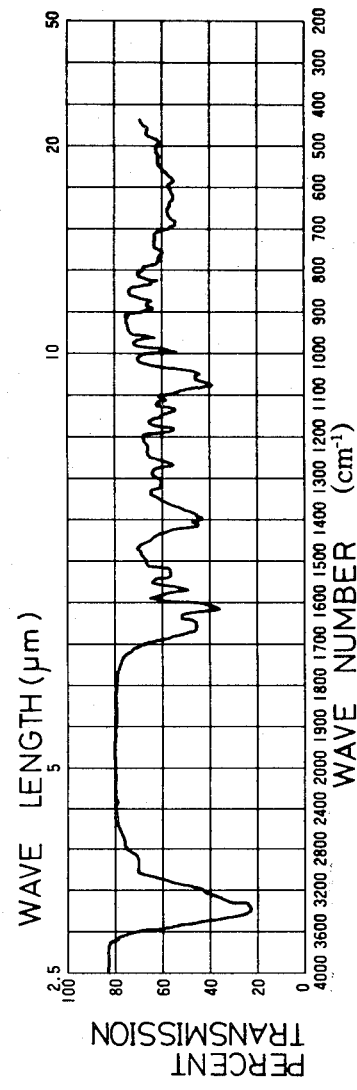
Figure 6:
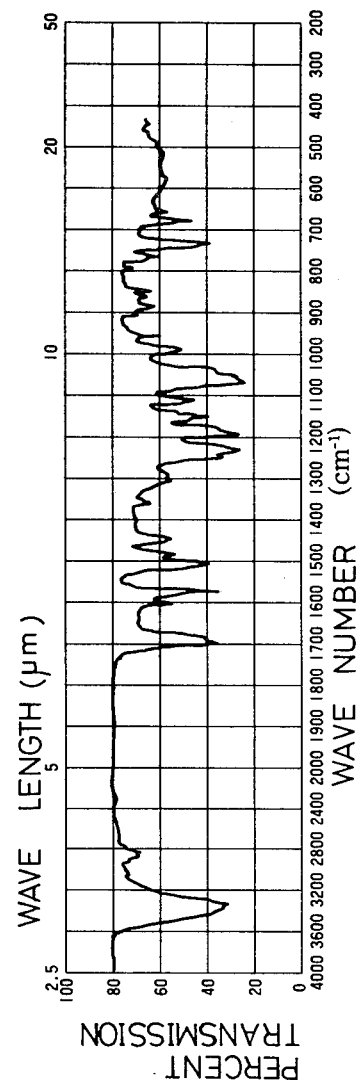
Figure 11:
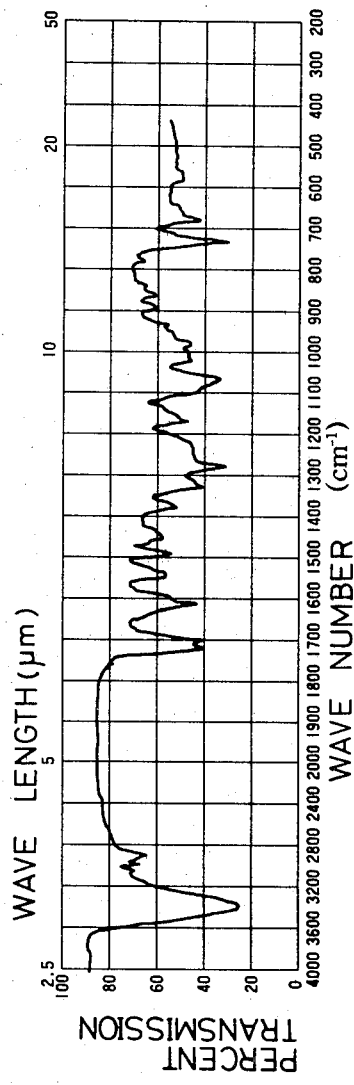
Figure 12:
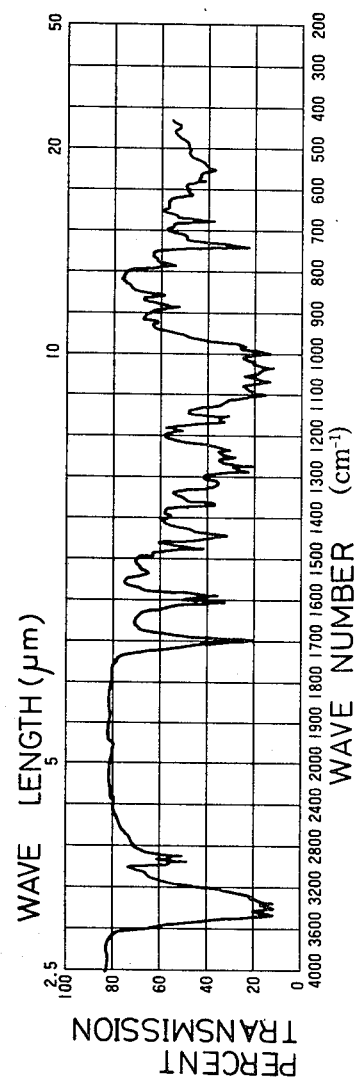
Figure 13:
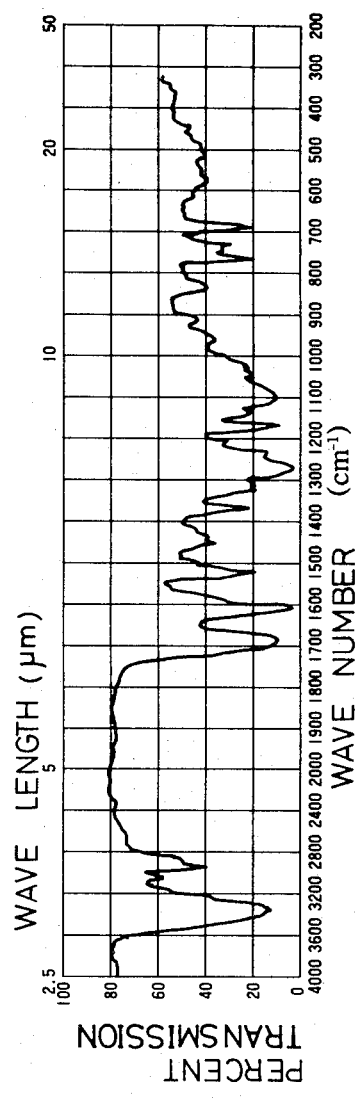
Figure 14:
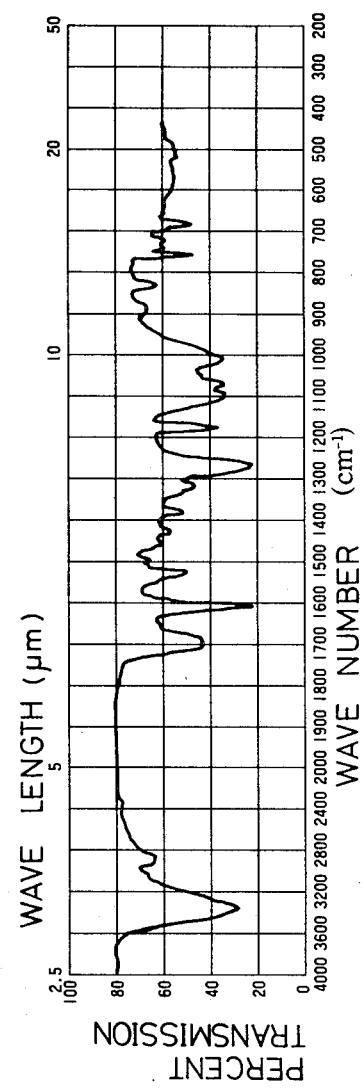
Figure 19:
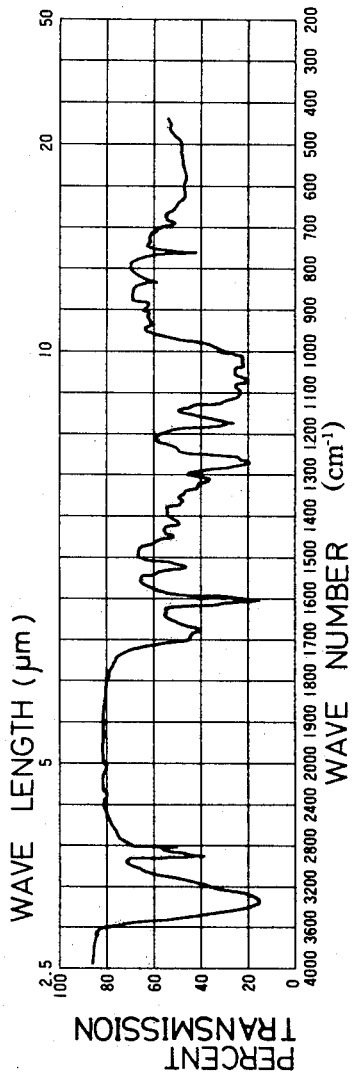
Figure 20:
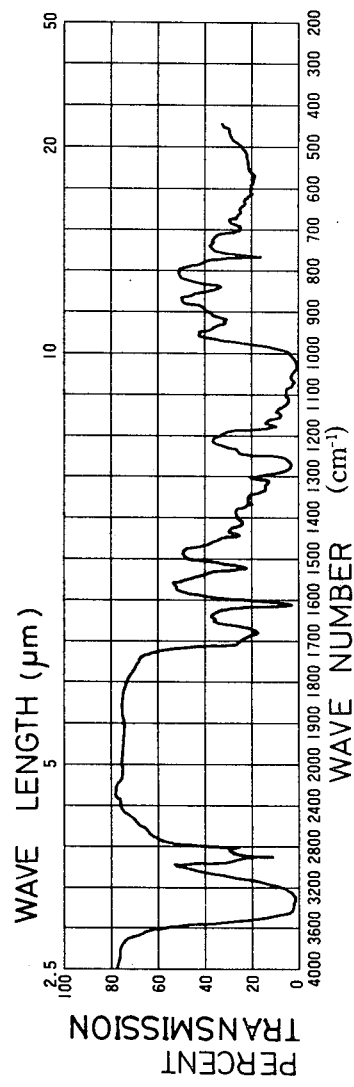
Figure 21:
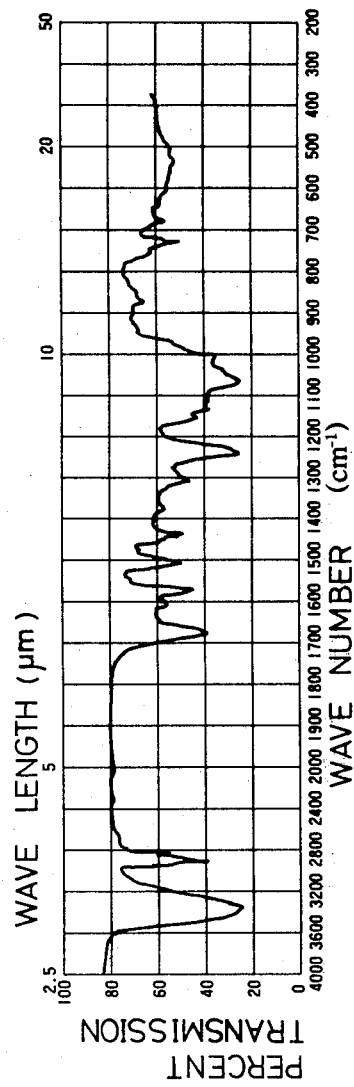
Figure 22:
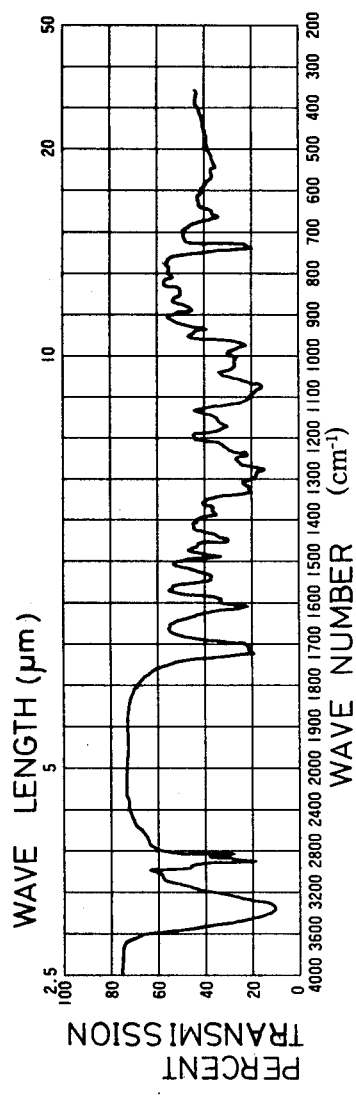
Figure 25:
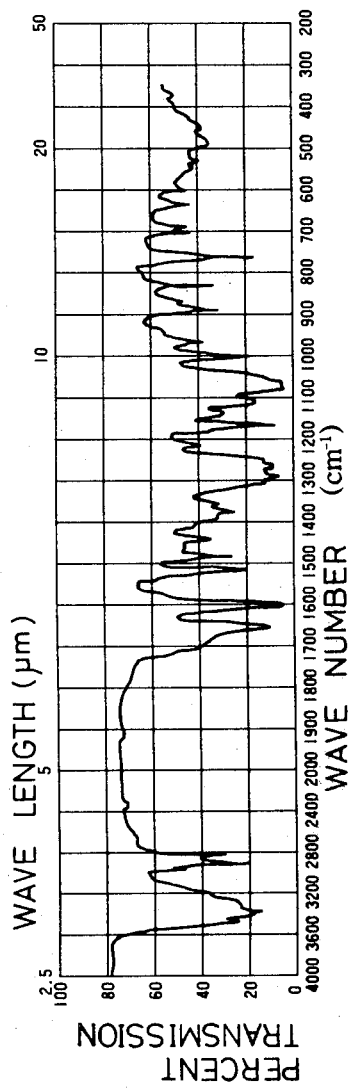
Figure 26:
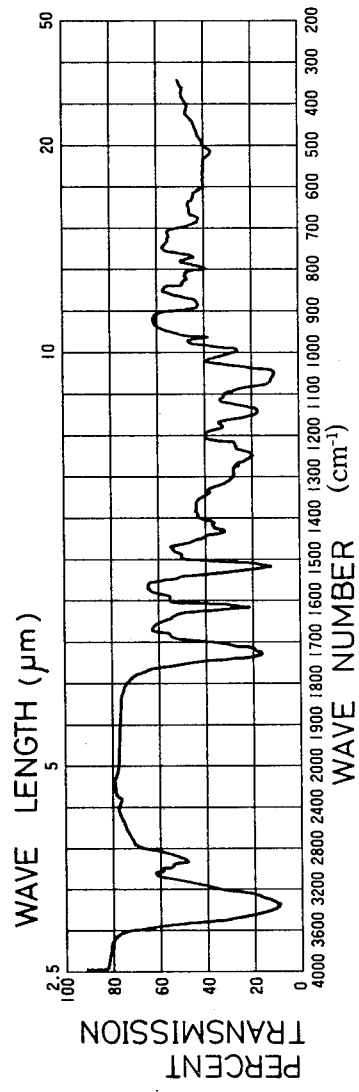
Figure 27:
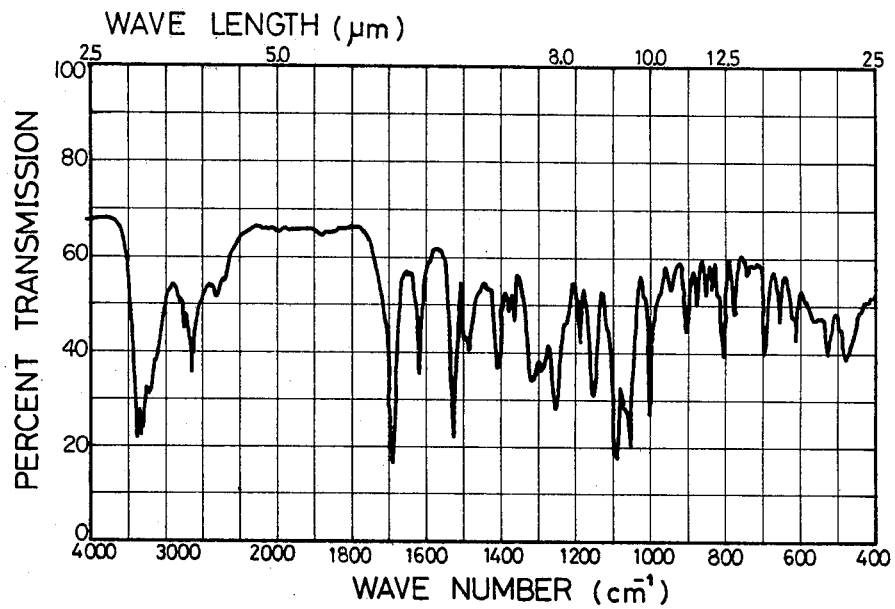
Figure 28:
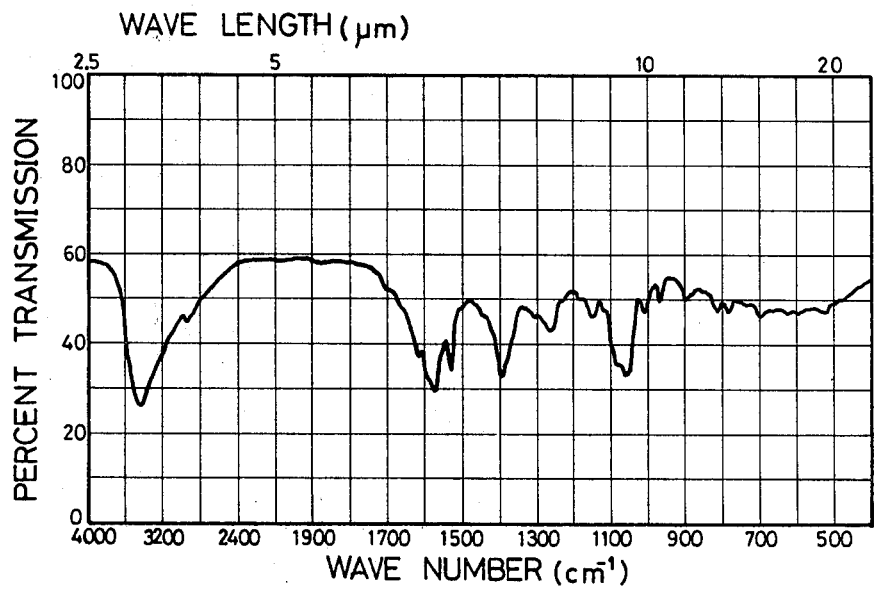
Figure 29:
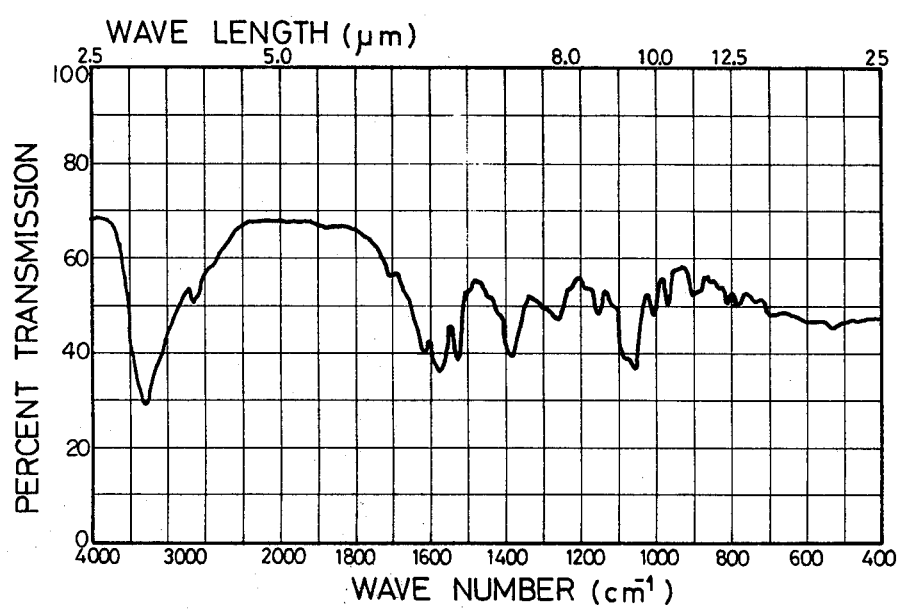

The object of the present invention is to provide novel derivatives of a saccharide having a suitability as a medicine because of their extremely low acute mammalian toxicity without exhibiting any side effects even after prolonged administration and having various physiological activities. Other objects of the present invention will be made clear from the following description:

The novel derivatives of a saccharide according to the present invention are represented by the following general formula (I):

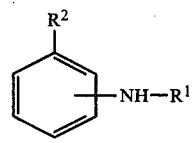

wherein $R^1$ represents a residue of mono-, di- or trisaccharide formed by removing one hydroxyl group at the reducing end of each of these saccharides; $R^2$ represents

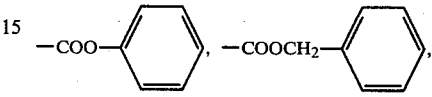

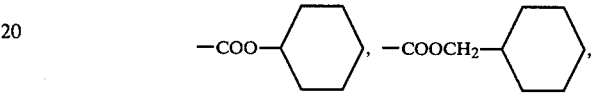

—CONH$_2$ or —CH$_2$COOR$^3$ and $R^3$ represents a hydrogen atom, a lower alkyl group or an equivalent of pharmaceutically acceptable metal.

The mono-, di- or trisaccharide of which the residue is represented by $R^1$ may be D-isomer, L-isomer, alpha-anomer, beta-anomer or a mixture of these anomers.

The mono-, di- and trisaccharide mentioned above include pentoses such as D-ribose, D-xylose, D- or L-arabinose, D-lyxose, L- or D-xylulose and D-ribulose, hexoses such as D- or L-galactose, D-glucose, D-mannose, D-fructose, L-sorbose, D-tagatose and D-psicose, heptoses such as D-mannoheptulose and D-sedoheptulose, disaccharides such as maltose, sucrose, cellobiose, lactose, laminaribiose, gentiobiose, melibiose, isomaltose, mannobiose and xylobiose, trisaccharides such as mannotriose, xylotriose, gentiotriose and maltotriose, aminosaccharides such as glucosamine, galactosamine, N-acetyl-D-glucosamine, and D-N-acetylmuramic acid, and deoxysaccharides such as 2-deoxy-D-ribose, 6-deoxygalactose, 6-deoxymannose and digitoxose. Moreover, in addition to the above-mentioned saccharides, $R^1$ of the general formula (I) includes also the residues of D-glucuronic acid and L-gulonic acid.

Besides, in the case where $R^2$ of the general formula (I) represents a group, —CH$_2$COOR$^3$ and $R^3$ represents a lower alkyl group or an equivalent of pharmaceutically acceptable metal, $R^3$ also includes alkali metals such as sodium and potassium, alkali earth metals such as calcium and magnesium, and aluminum, and still includes alkyl groups such as methyl-, ethyl-, propyl- and butyl group.

The derivative of a saccharide according to the present invention (hereinafter referred to as the present substance) is possibly produced by the following method:

In 2 to 200 ml of a solvent, for example, water, methanol, ethanol, acetone, chloroform, dioxan and dimethylformamide, 1 to 10 g of a saccharide is brought into reaction with 1 to 10 g of an ester of an aminobenzoic acid, an aminophenylacetic acid, an ester thereof or an aminobenzoic acid amide in the presence or in the absence of a catalyst at 20° to 200° C., preferably at 50° to 150° C. for 10 min. to 48 hours, preferably, for 30 min to 24 hours, and the thus obtained reaction mixture is cooled, or condensed after cooling to collect the thus deposited crystals followed by washing the collected crystals with water, methanol, acetone or ether and then by recrystallizing them.

Or else, namely, in cases where the present substance cannot be collected as crystals from the above-mentioned reaction mixture, the reaction mixture is subjected to the method of isolation such as thin layer chromatography or column chromatography to collect the present substance in a syruppy state or a powdery state.

The catalyst for use in the production of the present substance is preferably acetic acid, a salt thereof, hydrochloric acid or ammonium chloride, and the amount of the catalyst for use in the reaction is 0.1 to 5 g per 1 to 10 g of the saccharide, however, in the cases where the saccharide is disaccharide or trisaccharide, the use of ammonium chloride as the catalyst is not always favorable, but acetic acid is preferably used as the catalyst.

Besides, in cases where disaccharide or trisaccharide is used as the starting material, the use of 1 to 5 ml of acetic acid per 2 to 6 g of aminobenzoic acid amide, ester of aminobenzoic acid (including phenyl-, benzyl-, cyclohexyl- and hexa-hydrobenzyl esters) or aminophenylacetic acid (including lower alkyl ester thereof) in 2 to 200 ml of a solvent gives a favorable result. Use of a smaller amount of acetic acid causes reduction of the yield of the present substance, and on the other hand, use of the a greater amount of acetic acid does not give the improved yield.

In addition, in the case where the present substance to be prepared is represented by the general formula (I) wherein $R^3$ is represented by a group $-CH_2COOM$ in which M is an equivalent of a metal, the present substance is better to be prepared by substituting the hydrogen atom of the group $-CH_2COOH$ of the substance of which $R^3$ is represented by $-CH_2COOH$ following the well known method of substitution.

Some of the present substances and their physicochemical properties are exemplified in Table 1. As has been stated, the respective infrared absorption spectra of the present substances are shown in FIGS. 1 to 26, and the number of the present substances corresponds to the number of figures and to the number of examples, for example, FIG. 1 shows the infrared absorption spectrum of present substance No. 1 prepared in Example 1.

In the next place, toxicological properties of the present substances are shown as follows:

(1) Acute toxicity to mammals:

The oral toxicity of each of the present substances in Examples 1 to 26 was examined by administering orally each of them as a solution in distilled water or as a suspension in distilled water via a stomach tube to ICR-JCL mice forcibly by observing the mice's mortality for 7 days after the administration and by obtaining each value of $LD_{50}$ acute oral following the method of Litch-Field-Wilcoxon. The thus obtained values of the present substances produced in Examples 1 to 26, namely Compounds No. 1 to No. 26, are shown in Table 2. As are seen in Table 2, each of twenty six compounds of the present invention gives a large value of $LD_{50}$ showing that their acute oral toxicities are extremely low.

TABLE 1

Physicochemical properties of the present substances

| No. of Substance | Name of substance | Melting point (°C.) | Specific rotatory power (°)* | Elementary analytical composition (%) C | H | N | Ultra violet absorption max.** |
|---|---|---|---|---|---|---|---|
| 1 | o-Aminobenzoic acid amide-N—D-fructoside | 150–159 | −16.0 (C = 0.5, methanol) | 53.0 (53.1 | 6.0 6.1 | 8.3 8.2)*** | 225 and 250 |
| 2 | m-Aminobenzoic acid amide-N—cellobioside | 211–213 (decomp.) | −39.0 (C = 0.05, ethanol) | 48.1 (48.3 | 6.0 5.9 | 5.7 5.9) | 225, 245 and 310 |
| 3 | p-Aminobenzoic acid amide-N—D-xyloside | 184–186 (decomp.) | −32.0 (C = 0.2, methanol) | 53.7 (53.7 | 6.1 6.0 | 10.4 10.4) | 285 |
| 4 | p-Aminobenzoic acid amide-N—D-mannoside | 195–197 (decomp.) | −110.0 (C = 0.1, ethanol) | 53.0 (53.1 | 6.1 6.1 | 8.1 8.2) | 285 |
| 5 | p-Aminobenzoic acid amide-N—L-rhamnoside | 164–170 (decomp.) | −54.6 (C = 0.5, ethanol) | 55.2 (55.3 | 6.4 6.4 | 9.8 9.9) | 285 |
| 6 | Phenyl o-aminobenzoate-N—L-rhamnoside | 201–202 (decomp.) | −32.4 (C = 0.5, methanol) | 63.4 (63.5 | 5.9 5.8 | 4.0 3.9) | 223, 252 and 343 |
| 7 | Phenyl m-aminobenzoate-N—D-mannoside | 183–185 (decomp.) | −104 (C = 0.1, ethanol) | 60.8 (60.8 | 5.6 5.6 | 3.8 3.7) | 223, 245 and 320 |
| 8 | Phenyl p-aminobenzoate-N—D-xyloside | 77–72 | +4.4 (C = 0.5, methanol) | 60.7 (60.8 | 8.1 8.2 | 4.0 3.9) | 223, 296 |
| 9 | Phenyl p-aminobenzoate-N—cellobioside | 140–144 | −42.5 (C = 0.5, methanol) | 61.3 (61.3 | 6.5 6.3 | 2.9 2.9) | 223, 296 |
| 10 | Phenyl p-aminobenzoate-N—maltotrioside | 155–170 | +73.2 (C = 0.5, methanol) | 43.5 (43.5 | 7.0 7.1 | 2.5 2.4) | 223, 296 |
| 11 | Benzyl m-aminobenzoate-N—L-fucoside | 162–164 | +51.6 (C = 0.5, methanol) | 64.3 (64.3 | 6.4 6.2 | 3.7 3.8) | 226, 246 and 325 |
| 12 | Benzyl m-aminobenzoate-N—lactoside | 204–207 (decomp.) | −50.0 (C = 0.1, methanol) | 56.3 (56.4 | 6.2 6.3 | 2.6 2.5) | 226, 246 and 325 |

TABLE 1-continued

| No. of Substance | Name of substance | Melting point (°C.) | Specific rotatory power (°)* | Elementary analytical composition (%) C | H | N | Ultra violet absorption max.** |
|---|---|---|---|---|---|---|---|
| 13 | Benzyl p-aminobenzoate-N—D-deoxyriboside | — (syrup) | +34.6 (C = 0.45, methanol) | 66.4 (66.5 | 6.3 6.1 | 4.2 4.1) | 220, 290 |
| 14 | Benzyl p-aminobenzoate-N—D-glucoside | 88–95 | −43.2 (C = 0.5, methanol) | 61.8 (61.7 | 6.0 5.9 | 3.7 3.6) | 220, 290 |
| 15 | Benzyl p-aminobenzoate-N—D-fructoside | 90–98 | −148.0 (C = 0.25, methanol) | 62.1 (62.0 | 6.6 6.6 | 2.9 2.8) | 220, 290 |
| 16 | Cyclohexyl o-aminobenzoate-N—D-deoxyriboside | 153–155 | +3.2 (C = 0.5, ethanol) | 64.2 (64.3 | 7.5 7.7 | 4.2 4.2) | 222, 250 and 335 |
| 17 | Cyclohexyl m-aminobenzoate-N—D-mannoside | 161–166 | −40.0 (C = 0.1, methanol) | 59.8 (59.8 | 7.0 7.1 | 3.8 3.7) | 223, 245 |
| 18 | Cyclohexyl p-aminobenzoate-N—D-xyloside | 85–92 | −1.2 (C = 0.5, methanol) | 61.5 (61.5 | 7.2 7.1 | 4.1 4.0) | 220, 293 |
| 19 | Cyclohexyl p-aminobenzoate-N—cellobioside | 120–130 | −12.8 (C = 0.5, methanol) | 60.9 (60.9 | 7.1 7.1 | 2.7 2.8) | 220, 293 |
| 20 | Cyclohexyl p-aminobenzoate-N—maltotrioside | 158–165 | +68.4 (C = 0.5, methanol) | 52.8 (52.8 | 6.6 6.7 | 2.0 2.0) | 220, 293 |
| 21 | Hexahydrobenzyl m-aminobenzoate-N—lactoside | 147–157 | −2.8 (C = 0.25, methanol) | 56.0 (56.0 | 7.0 7.0 | 2.5 2.5) | 222, 250 and 337 |
| 22 | Hexahydrobenzyl m-aminobenzoate-N—L-fucoside | 115–123 | +43.6 (C = 0.5, methanol) | 63.1 (63.3 | 7.8 7.7 | 3.6 3.7) | 222, 245 |
| 23 | Hexahydrobenzyl p-aminobenzoate-N—D-riboside | 65–81 | +40.4 (C = 0.5, methanol) | 62.4 (62.5 | 7.4 7.4 | 3.8 3.8) | 221, 294 |
| 24 | Hexahydrobenzyl p-aminobenzoate-N—D-glucoside | 88–100 | −41.2 (C = 0.5, methanol) | 60.7 (60.8 | 7.3 7.3 | 3.5 3.5) | 221, 294 |
| 25 | Hexahydrobenzyl p-aminobenzoate-N—L-rhamnoside | 153–156 (decomp.) | +73.6 (C = 0.5, ethanol) | 63.3 (66.3 | 7.7 7.7 | 3.8 3.7) | 221, 294 |
| 26 | Methyl p-aminophenylacetate-N—L-rhamnoside | 88–100 | +48.4 (C = 0.5, methanol) | 57.7 (57.9 | 6.9 6.8 | 4.3 4.5 | 245 |
| 27 | p-Aminophenylacetic acid-N—L-rhamnoside | 137–139 | +16.7 (C = 1, methanol) | 56.31 (56.56 | 6.22 6.44 | 4.53 4.71) | 242, 288 |
| 28 | Sodium p-aminophenylacetate-N—L-rhamnoside | 144–146 | +15.9 (C = 1, water) | 52.75 (52.66 | 5.54 5.68 | 4.27 4.38) | 240, 287 |
| 29 | Potassium p-aminophenylacetate-N—L-rhamnoside | 134–137 | +17.4 (C = 1, water) | 50.10 (50.13 | 5.33 5.40 | 4.26 4.17) | 240, 288 |

Notes:
*$[\alpha]_D^{20}$ (°),
**(nm), and
***theoretical composition

TABLE 2:

Acute oral toxicities of the present substances (LD$_{50}$, g/kg)

| No. of compound | LD$_{50}$ | No. of compound | LD$_{50}$ |
|---|---|---|---|
| 1 | 11.8 | 15 | 11.0 |
| 2 | larger than 15.0 | 16 | 8.8 |
| 3 | larger than 15.0 | 17 | larger than 15.0 |
| 4 | 13.6 | 18 | larger than 15.0 |
| 5 | 10.5 | 19 | 14.6 |
| 6 | larger than 15.0 | 20 | 12.5 |
| 7 | 14.8 | 21 | larger than 15.0 |
| 8 | 13.5 | 22 | 10.1 |
| 9 | larger than 15.0 | 23 | 12.6 |
| 10 | 12.4 | 24 | 12.1 |
| 11 | 9.7 | 25 | 9.4 |
| 12 | 11.5 | 26 | 11.2 |
| 13 | 9.2 | 27 | 13.8 |
| 14 | 11.7 | 28 | 11.1 |
|  |  | 29 | 10.0 |
|  |  | mitomycin C | 0.023 |

(2) Anti-microbial activity:

Anti-microbial activity of the present substances was examined by culturing the following bacteria and fungi in a culture medium containing each one of twenty six substances of Examples 1 to 26.

The microbes were:

Bacteria: *Pseudomonas aeruginosa*, strain IAM 1514. *Escherichia coli*, strain IFO 12734. *Staphylococcus aureus*, strain 209P. *Bacillius subtilis*, strain IAM 1069.

Yeast: *Saccharomyces cerevisiae*, strain IAM 4207. *Candida albicans*, strain ATCC 752.

Fungi: *Trichophyton mentagrophytes*, strain IFO 6124. *Aspergillus niger*, strain IAM 3001.

The culture medium was prepared as follows:

A series of 2 times-dilution of each substance were prepared by dissolution or suspension into distilled water, and they were respectively added to 9 times by weight of Heart-infusion agar medium (for bacteria) or of Sabouraud's agar medium (for fungi) each kept warm, and then the mixture was poured into Petri dish to be used as culture plates. Preliminary cultured microbes were inoculated on the culture plates, and after culturing at 37° C. for 20 to 24 hours (for bacteria) or at 25° C. for 3 to 7 days (for fungi), the state of growth of the inoculated microbes was examined.

As the result, each substance of Examples 1 to 26 did not inhibit the microorganisms' growth at a concentration of 1 mg/ml.

(3) Mutagenicity:

The mutagenicity of each of 26 compounds of Examples 1 to 26 was examined by Rec-Assay, namely the growth inhibition to a recombination repair defficient strain M45 of *Bacillus subtilis*, and a recombination repair retaining strain H17 of *Bacillus subtilis*, cultured on B-II agar medium (consisting of 1 g of meat extract, 10 g of polypeptone, 5 g of sodium chloride, 15 g of agar and 1000 ml of disdilled water, adjusted to pH of 7.0) by making the micro-organism's streaks not mutually crossed at their starting point of the streaks on the culture plate. Then, a solution or suspension of each of the present compounds was absorbed on a round sheet of paper (disk) of 8 mm in diameter in an amount of 0.04 ml and the disk was placed on the culture plate so as to cover the starting points of the streaks of the microorganism's culture. After culturing overnight at 37° C., the length of inhibited growth of the micro-organism, while comparing those caused by a negative control of Kanamycin and a positive control of mitomycin C. The results are shown in Table 3. As is seen in Table 3, every compound of the present invention did not show a mutagenicity at a concentration as high as 500 microgram/disk.

TABLE 3:

| No. of Compound | Results of Rec-Assay of the present substances | | | |
|---|---|---|---|---|
| | Concentration (microgram/ disk) | Length of growth inhibition | | Difference (mm) |
| | | M45 (mm) | H17 (mm) | |
| 1 | 500 | 0 | 0 | 0 |
| 2 | 500 | 0 | 0 | 0 |
| 3 | 500 | 0 | 0 | 0 |
| 4 | 500 | 0 | 0 | 0 |
| 5 | 500 | 0 | 0 | 0 |
| 6 | 500 | 0 | 0 | 0 |
| 7 | 500 | 0 | 0 | 0 |
| 8 | 500 | 0 | 0 | 0 |
| 9 | 500 | 0 | 0 | 0 |
| 10 | 500 | 0 | 0 | 0 |
| 11 | 500 | 0 | 0 | 0 |
| 12 | 500 | 0 | 0 | 0 |
| 13 | 500 | 0 | 0 | 0 |
| 14 | 500 | 0 | 0 | 0 |
| 15 | 500 | 0 | 0 | 0 |
| 16 | 500 | 0 | 0 | 0 |
| 17 | 500 | 0 | 0 | 0 |
| 18 | 500 | 0 | 0 | 0 |
| 19 | 500 | 0 | 0 | 0 |
| 20 | 500 | 0 | 0 | 0 |
| 21 | 500 | 0 | 0 | 0 |
| 22 | 500 | 0 | 0 | 0 |
| 23 | 500 | 0 | 0 | 0 |
| 24 | 500 | 0 | 0 | 0 |
| 25 | 500 | 0 | 0 | 0 |
| 26 | 500 | 0 | 0 | 0 |
| 27 | 500 | 0 | 0 | 0 |
| 28 | 500 | 0 | 0 | 0 |
| 29 | 500 | 0 | 0 | 0 |
| Kanamycin | 10 | 6 | 3 | 3 |
| Mitomycin C | 0.05 | 12 | 1 | 11 |

(4) Delayed-type intracutaneous reaction:

In order to know the influence of the present compounds on the cellular immunity, a foot pad reaction test was carried out by using ICR-JCL mice as experimental animals and sheep erythrocyte as an antigen as follows:

Sheep erythrocytes were suspended in a physiological saline solution at a concentration of 10% by volume and 0.2 ml of the suspension was injected into the caudal vein of each mouse for the primary sensitization, and after 7 days, a 40% by volume suspension of the erythrocytes in physiological saline solution was injected into the foot pad of the mouse for the challenge. The thickness of the injected foot pad was measured on the next day. One of the present compounds was administered intraperitoneally at dose of 250 mg/kg/day once a day for continued 5 days around the day of the first sensitization as a center.

The thickness of the foot pad of the mouse administered with any of the present compounds showed no significant difference as compared to that of control animal (not administered with the present compound).

All the mice administered with mitomycin C at the same dose intraperitoneally died and accordingly, the determination was not possible.

(5) Productivity of antibody:

In order to know the influence of the present compounds on the humoral immunity, the following test was carried out:

A rat was sensitized by injecting 0.2 ml of a suspension of sheep erythrocytes in physiological saline at a concentration of 10% by volume in an amount of 0.2 ml from the caudal vein, and the blood of the mouse was collected after 7 days and tested by agglutination of the erythrocytes to see the productivity of the antibody. One of the present compounds was intraperitoneally administered for continued 5 days around the day of sensitization as a center. The results show that the agglutination value of the test animal was not different from that of control animal significantly.

Pharmaceutical properties:

(1) Anti-hyperglycemia activity (reduction of blood sugar level):

A group of Wistar rats to which at first streptozotocin was interperitoneally administered at a rate of 60 mg/kg and of which the positivity of glycosuria was confirmed after a week of the administration and to which regular insulin was further administered and of which the reduction of levels of glucose in urine and blood was once confirmed, however, of which hyperglycemia and hyperglycosuria were again confirmed after a few days was chosen and used as model animals of glycosuria in the following test. After orally administering each of the present compounds to the model animals at a dose of 300 mg/kg body weight, as a solution or dispersion in distilled water, the blood was collected two times, respectively after 3 and 6 hours of the administration. The level of glucose in the blood specimens was measured by an enzymatic method, the results being shown in Table 4.

TABLE 4:

| | Activity of reducing the level of blood sugar | | | | |
|---|---|---|---|---|---|
| | Reduced level of blood sugar after | | | unit: mg/dl Reduced level of blood sugar after | |
| No. of compound | 3 hrs. | 6 hrs. | No. of compound | 3 hrs. | 6 hrs. |
| 1 | 68 | 92 | 14 | 65 | 93 |
| 2 | 85 | 103 | 15 | 72 | 85 |
| 3 | 101 | 115 | 16 | 125 | 140 |
| 4 | 110 | 116 | 17 | 140 | 145 |
| 5 | 91 | 128 | 18 | 121 | 165 |
| 6 | 121 | 146 | 19 | 101 | 113 |
| 7 | 144 | 159 | 20 | 113 | 120 |
| 8 | 106 | 140 | 21 | 95 | 102 |
| 9 | 85 | 121 | 22 | 133 | 150 |
| 10 | 99 | 106 | 23 | 120 | 126 |
| 11 | 75 | 88 | 24 | 101 | 145 |
| 12 | 52 | 95 | 25 | 88 | 127 |
| 13 | 108 | 113 | 26 | 90 | 136 |
| | | | 27 | 91 | 90 |
| | | | 28 | 92 | 77 |
| | | | 29 | 88 | 71 |
| | | | Control | 21 | 19 |

(2) Anti-hypertension activity (reduction of blood pressure):

Rats of spontaneous hypertension were orally administered with each of the present compounds as a solution or dispersion in distilled water at a dose rate of 300 mg/kg body weight. After 3 and 6 hours of the administration, the blood pressure of each rat was determined, and the difference between the above-determined value and the value just before the administeration was used as the index of the activity of reducing the blood pressure of the compound. The results are shown in Table 5.

TABLE 5:

| | Activity of reducing the blood pressure | | | | |
|---|---|---|---|---|---|
| | Reduced level of blood pressure after | | | unit: mm Hg Reduced level of blood pressure after | |
| No. of compound | 3 hrs. | 6 hrs. | No. of compound | 3 hrs. | 6 hrs. |
| 1 | 16 | 19 | 14 | 24 | 24 |
| 2 | 20 | 22 | 15 | 18 | 20 |
| 3 | 20 | 24 | 16 | 20 | 20 |
| 4 | 14 | 20 | 17 | 23 | 28 |
| 5 | 17 | 18 | 18 | 22 | 25 |
| 6 | 22 | 23 | 19 | 20 | 21 |
| 7 | 24 | 26 | 20 | 22 | 24 |
| 8 | 18 | 20 | 21 | 16 | 17 |
| 9 | 25 | 28 | 22 | 15 | 21 |
| 10 | 18 | 18 | 23 | 21 | 22 |
| 11 | 21 | 25 | 24 | 19 | 21 |
| 12 | 16 | 18 | 25 | 16 | 18 |
| 13 | 20 | 21 | 26 | 20 | 23 |
| | | | 27 | 20 | 20 |
| | | | 28 | 25 | 19 |
| | | | 29 | 21 | 17 |

TABLE 5:-continued

| | Activity of reducing the blood pressure | | | | |
|---|---|---|---|---|---|
| | Reduced level of blood pressure after | | | unit: mm Hg Reduced level of blood pressure after | |
| No. of compound | 3 hrs. | 6 hrs. | No. of compound | 3 hrs. | 6 hrs. |
| | | | Control | −2* | 0 |

(3) Anti-tumour activity:

Sarcoma-180 was transplanted into the axillary part of ICR-JCL mice at a rate of $1 \times 10^6$ cells/animal, and after 24 hours of transplantation, each of the present compounds as a solution or dispersion in sterilized physiological saline solution was orally administered to each of the transplanted mice 10 times every other day at a dose of 500 mg/kg/time. On 25th day of the transplantation, tumour node(s) were extirpated from all the mice to determine the weight of the tumour nodes.

Antitumour activity (activity of inhibiting the proliferation of the transplanted sarcoma) of each of the present compounds was derived by the following formula and shown in Table 6:

Antitumour activity (Inhibiting rate, I.R.) = $(1 - T/C) \times 100(\%)$.

wherein

T represents the total weight of tumour nodes of the group of mice transplanted and administered with the present compound, and C represents the total weight of tumour nodes of the group of mice transplanted, however, not administered with any agents.

TABLE 6:

| | Antitumour activity against Sarcoma-180 | | |
|---|---|---|---|
| No. of compound | I.R. %* | No. of compound | I.R. % |
| 1 | 42 | 14 | 42 |
| 2 | 35 | 15 | 43 |
| 3 | 47 | 16 | 37 |
| 4 | 42 | 17 | 49 |
| 5 | 39 | 18 | 62 |
| 6 | 44 | 19 | 51 |
| 7 | 49 | 20 | 37 |
| 8 | 53 | 21 | 44 |
| 9 | 40 | 22 | 35 |
| 10 | 39 | 23 | 47 |
| 11 | 40 | 24 | 40 |
| 12 | 37 | 25 | 50 |
| 13 | 38 | 26 | 45 |
| | | 27 | 43 |
| | | 28 | 45 |
| | | 29 | 38 |

Note:
*Inhibition rate or the rate of inhibiting the growth of the sarcoma.

(4) Anti-hyperlipemia activity (reducing the level of lipids in blood):

Japanese white male rabbits were fed for 3 months with a solid diet containing 1% of cholesterol taken ad lib, and after confirming the raised lipid content of the serum of the rabbits, they were utilized as model animals suffering from experimental arteriosclerosis. Each of the present compounds was administered orally as a solution or dispersion in distilled water to the experimental animals of each group at a dose rate of 300 mg/kg once, and blood samples were taken at a predetermined time interval from the auricular vein of each animal. The content of cholesterol in the blood specimen was traced as the time passed by, with an enzymatic method, and the content of beta-lipoprotein in the same blood specimen was traced with a colorimetry. The results of tracing are shown in Table 7. Each value in Table 7 is the difference between the level just before administration and the level after 3 or 6 hours of the administration.

TABLE 7:

Anti-hyperlipemia activity (reducing the levels of total cholesterol and beta-lipoprotein in blood)

| No. of compound | Reduction of cholesterol level (mg/dl) after | | Reduction of beta-lipoprotein level (mg/dl) after | |
|---|---|---|---|---|
| | 3 hrs. | 6 hrs. | 3 hrs. | 6 hrs. |
| 1 | −2 | 36 | 120 | 131 |
| 2 | 1 | 30 | 108 | 124 |
| 3 | 3 | 45 | 115 | 119 |
| 4 | 0 | 46 | 123 | 135 |
| 5 | −1 | 32 | 134 | 148 |
| 6 | 4 | 57 | 152 | 155 |
| 7 | −2 | 62 | 141 | 150 |
| 8 | 6 | 46 | 128 | 144 |
| 9 | −1 | 40 | 126 | 136 |
| 10 | −5 | 33 | 106 | 111 |
| 11 | −1 | 50 | 98 | 109 |
| 12 | 7 | 48 | 121 | 124 |
| 13 | 4 | 35 | 135 | 144 |
| 14 | 3 | 38 | 143 | 146 |
| 15 | −1 | 45 | 150 | 154 |
| 16 | 0 | 33 | 104 | 110 |
| 17 | −2 | 40 | 124 | 136 |
| 18 | 2 | 62 | 148 | 154 |
| 19 | 3 | 41 | 135 | 148 |
| 20 | −2 | 50 | 125 | 128 |
| 21 | 4 | 43 | 96 | 109 |
| 22 | 6 | 38 | 125 | 133 |
| 23 | −1 | 40 | 141 | 143 |
| 24 | 2 | 32 | 95 | 111 |
| 25 | −3 | 44 | 95 | 106 |
| 26 | −3 | 51 | 123 | 133 |
| 27 | 1 | 30 | 125 | 130 |
| 28 | 5 | 25 | 101 | 100 |
| 29 | 3 | 40 | 95 | 121 |
| Control | −3 | 0 | −1 | −4 |

Note:
denotes the raising of cholesterol level or the raising of beta-lipoprotein level.

(5) Anti-inflammatory diseases:
(5-1) Anti-Carrageenin edema activity:

After orally administering each of the present compounds forcibly to each group of rats, composed of 10 animals, as a solution or dispersion in distilled water at a dose of 1000 mg/kg once, 0.1 ml of an aqueous dispersion of 1% carrageenin in aqueous physiological saline solution was injected into the foot pad of the right hind leg of the administered animal following Van Arman et al. (1963). Thereafter, the thickness of the foot pad was measured at a time interval to find the rate of inhibiting of the swelling of the foot pad according to the following formula:

Rate of inhibition (I.R.) (%) = (1−T/C)×100 wherein

T means the average volume of the foot pad of the animals administered with one of the present compounds and carrageenin, and C means that of the animal not administered with the present compound, however, administered with carrageenin. The thus obtained I.R. (%) is shown in Table 8.

(5-2) Anti-granuloma activity:

Following the method of Winter et al. (1963), each two cotton wool pellets, each weighing 30±1 mg, were implanted into the back of each rats of groups of rats, each group consisting of 6 animals, at the positions of mutually symmetrical concerning the median line of the rat. To these groups of the thus operated rats, the present compounds were respectively administered orally and forcibly as a solution or dispersion in distilled water for 7 continuous days, once a day at a dose of 1000 mg/kg/day. On 8th day of the implantation, the granuloma was extirpated and the dry weight of the granuloma was measured, the rate of inhibiting the proliferation of granuloma being obtained as in (5-1) being shown in Table 8.

(5-3) Anti-exudation activity:

Following the method of Baris et al. (1965), air was injected subcutaneously into the back of groups of rats, each group consisting of 6 animals to make an air pouch, and 0.5 ml of sesame oil containing 1% by weight of croton oil was injected into the air pouch. Each of the present compounds was orally administered forcibly to each of the groups of rats as a solution or dispersion in distilled water at a dose rate of 1000 mg/kg/day for continued five days. The amount of liquid exudated into the air pouch was measured on 6th day of the operation. The rate of inhibiting the exudation of the liquid was obtained by the same manner as in (5-2) and the results are shown also in Table 8.

TABLE 8:

Antiinflammatory activities of the present substances

Unit: Inhibiting Ratio (I.R.) %

| No. of compound | I.R. against carageenin edema | I.R. against cotton pellet edema | I.R. against exudation |
|---|---|---|---|
| 1 | 15.6 | 6.6 | 17.5 |
| 2 | 20.3 | 6.1 | 6.6 |
| 3 | 26.5 | 7.0 | 19.1 |
| 4 | 12.1 | 14.9 | 5.7 |
| 5 | 4.2 | 16.8 | 12.4 |
| 6 | 7.6 | 20.5 | 19.0 |
| 7 | 5.9 | 25.3 | 7.5 |
| 8 | 21.4 | 5.6 | 15.7 |
| 9 | 3.7 | 7.9 | 18.8 |
| 10 | 6.6 | 19.6 | 7.5 |
| 11 | 22.8 | 4.4 | 11.0 |
| 12 | 18.7 | 8.4 | 10.7 |
| 13 | 7.0 | 4.2 | 23.5 |
| 14 | 5.1 | 23.3 | 6.9 |
| 15 | 30.8 | 9.0 | 7.5 |
| 16 | 18.6 | 6.5 | 5.7 |
| 17 | 4.3 | 19.7 | 14.6 |
| 18 | 19.7 | 12.2 | 25.0 |
| 19 | 5.5 | 5.5 | 24.6 |
| 20 | 8.6 | 21.7 | 6.2 |
| 21 | 19.4 | 7.2 | 20.7 |
| 22 | 24.6 | 15.7 | 7.7 |
| 23 | 4.9 | 7.3 | 22.5 |
| 24 | 10.6 | 16.9 | 8.7 |
| 25 | 18.1 | 6.5 | 22.3 |
| 26 | 5.3 | 24.1 | 17.7 |
| 27 | 5.2 | 23.1 | 16.5 |
| 28 | 8.3 | 20.6 | 6.1 |
| 29 | 9.3 | 15.9 | 5.8 |
| Control | 0 | 0 | 0 |

(6) Analgetic activity:
(6-1) Against mechanical stimulation of pressure:

ICR female mice showing the threshold value of pain of 50 to 80 mmHg when the base of its tail is subjected to pressure of a pressure-stimulation apparatus of Takagi and Kameyama et al. were chosen as the experimental animals, and after administering orally 1000 mg/kg of one of the present compounds, the above-mentioned pressure test was repeatedly carried out as the time passed by to find the pressure and the time until the animal showed a pseudo-escaping reaction for evaluating the analgetic activity of the compound. The results are shown in Table 9.

(6-2) Against chemical stimulation of acetic acid:

After 30 min of oral administration of one of the present compounds at a dose of 1000 mg/kg to a group of ICR female mice of 5 to 6 weeks after birth, a group being consisted of 10 animals, an aqueous 0.6% acetic acid solution was intraperitoneally injected to the mouse in an amount of 0.1 ml/10 g of body weight of the mouse, and then, the number of occurrence of writhing was counted for 10 min by the method of Kostet, et al. The rate of inhibition of the writhing was calculated by the following formula and shown also in Table 9:

Rate of inhibition (I.R.) (%) = $(1 - T/C) \times 100$ wherein

T represents the average number of writhing of the group of mice administered with the present compound and injected with acetic acid, and C represents the average number of writhing of the group of mice only injected with acetic acid (control).

The results are also shown in Table 9.

TABLE 9:

| No. of compound | Analgetic activity against physical stimulation | | I.R. of writhing (%) |
|---|---|---|---|
| | Pseudo-escapting reaction | | |
| | pressure (mmHg) | time (sec) | |
| 1 | 78 | 38 | 17 |
| 2 | 84 | 42 | 20 |
| 3 | 93 | 44 | 22 |
| 4 | 96 | 45 | 41 |
| 5 | 90 | 41 | 52 |
| 6 | 98 | 43 | 37 |
| 7 | 95 | 44 | 46 |
| 8 | 80 | 39 | 20 |
| 9 | 86 | 38 | 28 |
| 10 | 86 | 36 | 30 |
| 11 | 74 | 35 | 17 |
| 12 | 90 | 42 | 33 |
| 13 | 82 | 40 | 24 |
| 14 | 92 | 44 | 39 |
| 15 | 78 | 37 | 19 |
| 16 | 87 | 39 | 26 |
| 17 | 92 | 42 | 47 |
| 18 | 94 | 39 | 33 |
| 19 | 82 | 37 | 24 |
| 20 | 75 | 35 | 17 |
| 21 | 84 | 40 | 28 |
| 22 | 75 | 37 | 19 |
| 23 | 80 | 39 | 23 |
| 24 | 85 | 42 | 41 |
| 25 | 93 | 44 | 50 |
| 26 | 92 | 41 | 34 |
| 27 | 91 | 40 | 35 |
| 28 | 87 | 38 | 25 |
| 29 | 84 | 41 | 26 |
| Control | 68 | 31 | 0 |

(7) Anti-pyrexia activity:

Following the method of Winter et al. (1961), an aqueous dispersion of 20% by weight of *Saccharomyces cerevisiae* was subcutaneously injected into groups of rats, each group consisting of 6 animals, and after 10-hour fasting, 1000 mg/kg of each of the present compounds was orally administered to the rat as a solution of dispersion in distilled water, and then the rectal temperature of the rat was measured at a predetermined interval of time to find the lowest temperature.

The anti-pyrexia activity of each compound was obtained from the following formula:

Anti-pyrexia activity represented by the rate of inhibition (I.R.) (%) = $(C_1 - T)/(C_1 - C_2) \times 100$, wherein $C_2$ represents the average rectal temperature of negative control (non-treatment), not injected with the yeast and not administered with the present compound, $C_1$ represents the average temperature of positive control, injected with the yeast and not administered with the compound and T represents the temperature of tested animals, injected with the yeast and administered with the present compound.

The results are shown in Table 10.

As is seen in Table 10, the present compounds exhibited the antipyretic activity.

TABLE 10:

| No. of compound | Anti-pyrexia activity of the present substances | | |
|---|---|---|---|
| | Rate of inhibiting pyrexia (I.R.) (%) | No. of compound | Rate of inhibiting pyrexia (I.R.) (%) |
| 1 | 41 | 14 | 56 |
| 2 | 36 | 15 | 26 |
| 3 | 20 | 16 | 48 |
| 4 | 28 | 17 | 30 |
| 5 | 59 | 18 | 62 |
| 6 | 69 | 19 | 37 |
| 7 | 31 | 20 | 23 |
| 8 | 47 | 21 | 28 |
| 9 | 32 | 22 | 29 |
| 10 | 41 | 23 | 15 |
| 11 | 29 | 24 | 48 |
| 12 | 17 | 25 | 54 |
| 13 | 39 | 26 | 60 |

As is seen in the tabulated data of the pharmacological properties, each of the present compounds has a therapeutic activity against hyperglycemia, hypertension, arteriosclerosis, tumour, pains, pyrexia and inflammatory diseases, and in addition, its toxicity to mammals is very low, therefore, any of the present compounds can be effectively applicable in treating the above-mentioned diseases.

In the next place, the formulation of the present compound into pharmaceutical compositions is described as follows:

In the case where any of the present compounds is applied as a pharmaceutical for treating hyperglycemia, hypertension, tumours, arteriosclerosis, inflammatory diseases or stimulation on central nerve system resulting in pains, it may be possible to administer one of the present compounds in a state suitable for obtaining its effectiveness corresponding to the kinds and symptoms of the above-mentioned diseases, and the compound may be singly or after formulating into a pharmaceutical composition with pharmaceutically acceptable carriers, adjuvants or other pharmaceutical(s) applied in dose unit form.

As the dose unit form, the present compounds can take the orally administrable forms such as powder, granule, tablet, sugar-coated tablet, capsuled states, syrup, spherical particle, suspension in medium, solution in solvent or emulsion in medium, and parenterally administrable forms such as injection contained in ampoule or in vial and suppository. The state of the above-mentioned diluent may be solid, liquid and semisolid, and conventionally used carriers or diluents such as excipient, vehicle, binding agent, wetting agent, disintegrating agent, surfactant, lubricant, dispersing agent, buffering agent, perfume, preservative, dissolution agent, solvent, etc. are suitably utilized.

Concrete examples of the diluent (carrier and adjuvant) which may be exemplified are: lactose, sucrose, sorbitol, mannitol, starch, precipitated calcium carbonate, heavy magnesium oxide, talc, calcium stearate, magnesium stearate, cellulose and derivatives thereof, amylopectin, polyvinyl alcohol, gelatin, surfactants, water, aqueous physiological saline solution, ethanol, glycerin, propylene glycol, cacao butter, laurin fat, vaseline, paraffin, and higher alcohols.

The pharmaceutical composition containing the present compound as an active ingredient may be prepared by any of the publicly known methods, and the content of the present compound as the active ingredient in the pharmaceutical composition is generally 0.01 to 100% by weight, preferably from 0.05 to 80% by weight. The pharmaceutical composition for use in treating the afore-mentioned diseases may be administered orally or parenterally, however, preferably it is administered orally. The oral administration includes sublingual one. The parenteral administration includes subcutaneous-, muscular-, intravenal- and drip administration, and rectal administration.

Since the dose rate of the present compound depends on the species, the age, the sex, the personal difference and the conditions of the disease, there may be cases where an amount larger or smaller than the under-mentioned one is administered, however, generally in the human cases, the oral dose rate is 0.1 to 500 mg/kg body weight/day, preferably 1 to 250 mg/kg/day, and the parenteral dose rate is 0.01 to 200 mg/kg/day, preferably, 0.1 to 100 mg/kg/day, and the amount is divided into 1 to 4 portions and one portion is administered at a time.

The present compounds and the pharmaceutical compositions containing one of the present compounds are exemplified by the following non-limitative examples and formulation examples:

EXAMPLE 1

Synthesis of o-aminobenzoic acid amide-N-D-fructoside:

Into 30 ml of ethanol, 2.3 g of o-aminobenzoic acid amide, 2.7 g of D-fructose and a few drops of concentrated hydrochloric acid were added, and the mixture was heated under a reflux condenser to bring the raw materials into condensation. Then the reaction mixture was condensed and poured into an excess acetone. The thus separated precipitate was collected by filtration and dried to obtain a powdery substance yellowish brown in colour in a yield of 44%.

EXAMPLE 2

Synthesis of m-aminobenzoic acid amide-N-cellobioside:

A solution containing 5.1 g of cellobiose dissolved in 18 ml of water and a solution of 2.1 g of m-aminobenzoic acid amide dissolved in 8 ml of ethanol were mixed, and after adding 2 ml of acetic acid into the mixture, the whole mixture was heated under a reflux condenser to bring into condensation. By repeated recrystallization of the reaction mixture from a mixture of water and methanol, colourless and needle-like crystals were obtained in a yield of 26%.

EXAMPLE 3

Synthesis of p-aminobenzoic acid amide-N-D-xyloside:

In 30 ml of an aqueous 94% ethanolic solution, 2.8 g of p-aminobenzoic acid amide, 3.0 g of D-xylose and 0.3 g of ammonium chloride were heated under a reflux condenser to bring into condensation, and 10 ml of the solvent was added during the condensation to facilitate the stirring. After cooling the reaction mixture, the separated crystals were repeatedly recrystallized from a mixture of water and methanol to obtain colourless needle-like crystals in a yield of 44%.

EXAMPLE 4

Synthesis of p-aminobenzoic acid amide-N-D-mannoside:

In 25 ml of an aqueous 94% by weight of ethanolic solution, 2.1 g of p-aminobenzoic acid amide, 2.5 g of D-mannose and 0.2 g of ammonium chloride were heated under a reflux condenser to obtain a white precipitate. The crystalline precipitate obtained by filtration of the reaction mixture was repeatedly recrystallized from an aqueous 94% ethanolic solution to obtain colourless needle-like crystals in a yield of 94%.

EXAMPLE 5

Synthesis of p-aminobenzoic acid amide-N-L-rhamnoside:

In 25 ml of an aqueous 94% ethanolic solution, 2.3 g of p-aminobenzoic acid amide, 2.7 g of L-rhamnose and 0.2 g of ammonium chloride were heated under a reflux condenser to bring into condensation. The reaction mixture thus obtained was left overnight in an ice-box. The separated crystals were collected and subjected to repeated recrystallization from an aqueous 94% ethanolic solution to obtain colourless needle-like crystals in a yield of 68%.

EXAMPLE 6

Synthesis of phenyl o-aminobenzoate-N-L-rhamnoside:

In 25 ml of an aqueous 94% ethanolic solution, 3.2 g of phenyl o-aminobenzoate, 2.7 g of L-rhamnose and 0.2 g of ammonium chloride were heated under a reflux condenser to bring into condensation. After condensing and cooling the reaction mixture, the separated crystals were collected and recrystallized repeatedly from an aqueous 94% ethanolic solution to obtain colourless needle-like crystals in a yield of 35.5%.

EXAMPLE 7

Synthesis of phenyl m-aminobenzoate-N-D-mannoside:

In 25 ml of an aqueous 94% ethanolic solution, 3.0 g of phenyl m-aminobenzoate, 2.5 g of D-mannose and 0.2 g of ammonium chloride were heated under a reflux condenser to bring into condensation. The crystals which separated after cooling the reaction mixture were repeatedly recrystallized from an aqueous 94% ethanolic solution to obtain colourless needle-like crystals in a yield of 66.7%.

EXAMPLE 8

Synthesis of phenyl p-aminobenzoate-N-D-xyloside:

In 30 ml of an aqueous 94% ethanolic solution, 3.2 g of phenyl p-aminobenzoate, 2.3 g of D-xylose and 0.2 g of ammonium chloride were heated under a reflux condenser. After condensing the reaction mixture to ⅓ time by volume, the condensate was shaken with an addition of ether and water. The thus separated aqueous layer was extracted with ethyl acetate repeatedly and the layer of ethyl acetate was condensed under a reduced pressure and dried to obtain a yellowish brown powdery material as the object in a yield of 23%.

EXAMPLE 9

Synthesis of phenyl p-aminobenzoate-N-cellobioside:

An aqueous solution of 5.1 g of cellobiose dissolved in 13 ml of water and a solution of 3.2 g of phenyl p-aminobenzoate dissolved in 10 ml of ethanol were mixed and after adding 3.3 ml of acetic acid to the mixture, the whole mixture was heated under a reflux condenser to bring the raw materials into condensation. After condensing and letting the reaction mixture alone, the separated crystals of cellobiose were removed, and the filtrate was subjected to thin layer chromatography and eluted by a solvent mixture of methanol, benzene, butanol and water of a mutual radio of 5:5:10:2 by volume. The eluate was again subjected to the chromatography to purify the product and a slightly yellowish powdery substance was obtained in a yield of 12.5%.

EXAMPLE 10

Synthesis of phenyl p-aminobenzoate-N-maltotrioside:

An aqueous solution of 5.0 g of maltotriose dissolved in 2.8 ml of water and a solution of 2.1 g of phenyl p-aminobenzoate dissolved in 8.5 ml of ethanol were mixed, and after adding 1.4 ml of acetic acid to the mixture, the whole mixture was heated under a reflux condenser to bring the raw materials into condensation. The reaction mixture was condensed to dryness and dissolved into an aqueous 50% ethanolic acid, and the solution was poured into an excess acetone to separate the object product out from the mixture. The thus separated precipitate was dissolved into an aqueous 50% ethanolic solution and the solution was subjected to thin layer chromatography using a silicagel plate. The adsorbed product was eluted by a solvent mixture of methanol, benzene, butanol and water of a volume ratio of 5:5:10:2. The eluate was again subjected to the same chromatography to separate and obtain the product as a pale yellow powdery substance in a yield of 5.2%.

EXAMPLE 11

Synthesis of benzyl m-aminobenzoate-N-L-fucoside:

In 20 ml of an aqueous 94% ethanolic solution, 2.1 g of benzyl m-aminobenzoate, 1.5 g of L-fucose and 0.2 g of ammonium chloride were heated under a reflux condenser to bring the raw materials into condensation, and the reaction mixture was condensed. The condensate was poured into an excess acetone, and the insoluble matter was removed by filtration. The filtrate was evaporated to dryness, and after dissolving the dried solid into an aqueous 50% ethanolic solution, the solution was subjected to thin layer chromatography using a silicagel plate. The adsorbed substance was eluted by a solvent mixture of methanol, benzene, butanol and water of a volume ratio of 5:5:10:2 and the eluate was again subjected to the same chromatography to obtain the object product as a pale yellow powdery material in a yield of 19%.

EXAMPLE 12

Synthesis of benzyl m-aminobenzoate-N-lactoside:

An aqueous solution of 3.6 g of lactose dissolved in 10 ml of water and a solution of 2.3 g of benzyl m-aminobenzoate dissolved in 5.5 ml of ethanol were mixed, and after adding 1.4 ml of acetic acid into the mixture, the whole mixture was heated under a reflux condenser to bring the raw materials into condensation. After cooling the reaction mixture, the thus separated precipitate was collected by filtration and recrystallized several times from a solvent mixture of methanol, water and dioxane to obtain needle-like crystals in a yield of 22.7%.

EXAMPLE 13

Synthesis of benzyl p-aminobenzoate-N-D-deoxyriboside:

In 25 ml of an aqueous 94% ethanolic solution, 3.4 g of benzyl p-aminobenzoate, 2.0 g of D-deoxyribose and 0.2 g of ammonium chloride were heated under a reflux condenser to bring the raw materials into condensation, and the reaction mixture was condensed and poured into acetone. After filtrating the mixture, the filtrate was dried to solid. Then, the solid was subjected to the procedures similar to those of Example 11 to obtain a yellowish brown syrup in a yield of 10%.

EXAMPLE 14

Synthesis of benzyl p-aminobenzoate-N-D-glucoside:

In a similar manner as in Example 13 except using 2.7 g of D-glucose in 30 ml of an aqueous 94% ethanolic solution instead 2.0 g of D-deoxyribose in 25 ml of the solvent, a faintly yellow powdery substance was obtained in a yield of 9.4%.

EXAMPLE 15

Synthesis of benzyl p-aminobenzoate-N-D-fructoside:

In a similar manner as in Example 14 except for using D-fructose instead of D-glucose, a reaction of condensation was carried out, and the reaction mixture was condensed to dryness. The dried solid was dissolved in methanol while heating. After separating the crystals which precipitated on cooling the solution, the filtrate was condensed, and extracted with water and ethyl acetate. After condensing the organic layer, the condensate was subjected to thin layer chromatography using a silicagel plate while eluting with a solvent mixture of methanol, benzene, butanol and water of a volume ratio of 5:5:10:2. The eluate was again subjected to the same chromatography to obtain a yellow powdery substance in a yield of 2%.

EXAMPLE 16

Synthesis of cyclohexyl o-aminobenzoate-N-D-deoxyriboside:

In 25 ml of an aqueous 94% ethanolic solution, 3.3 g of cyclohexyl o-aminobenzoate, 2.0 g of D-deoxyribose and 0.2 g of ammonium chloride were heated under a reflux condenser to bring the raw material into condensation. The reaction mixture was dried to solid, and the solid was dissolved in methanol by heating. After collecting the crystals precipitated on cooling the methanolic solution, the crystals were repeatedly recrystallized from a mixture of methanol, acetone and water to obtain colourless and needle-like crystals in a yield of 17.9%.

EXAMPLE 17

Synthesis of cyclohexyl m-aminobenzoate-N-D-mannoside:

In 25 ml of an aqueous 94% ethanolic solution, 3.1 g of cyclohexyl m-aminobenzoate, 2.5 g of D-mannose and 0.2 g of ammonium chloride were heated under a reflux condenser to bring the raw materials into condensation. After letting the reaction mixture to cooling, the precipitated crystals were collected by filtration and repeatedly recrystallized from an aqueous 94% ethanolic solution to obtain flaky crystals in a yield of 91.6%.

EXAMPLE 18

Synthesis of cyclohexyl p-aminobenzoate-N-D-xyloside:

In 30 ml of an aqueous 94% ethanolic solution, 3.3 g of cyclohexyl p-aminobenzoate, 2.3 g of D-xylose and 0.2 g of ammonium chloride were heated under a reflux condenser to bring the raw materials into condensation. After condensing the reaction mixture, the condensate was poured into an excess acetone followed by removing the thus precipitated matter by filtration. The filtrate was dried to solid and the solid was dissolved in an aqueous 50% methanolic solution, the solution being subjected to thin layer chromatography as in Example 9 to obtain a pale yellow powdery substance in a yield of 8%.

EXAMPLE 19

Synthesis of cyclohexyl p-aminobenzoate-N-cellobioside:

An aqueous solution of 5.1 g of cellobiose dissolved in 13 ml of water and a solution of 3.3 g of cyclohexyl p-aminobenzoate dissolved in 10 ml of ethanol were mixed, and after adding 3.3 ml of acetic acid into the mixture, the whole mixture was heated under a reflux condenser to bring the raw materials into condensation. The reaction mixture was treated as in Example 11 to obtain a pale yellow powdery substance in a yield of 4.9%.

EXAMPLE 20

Synthesis of cyclohexyl p-aminobenzoate-N-maltotrioside:

An aqueous solution of 5.0 g of maltotriose dissolved in 4 ml of water and a solution of 2.2 g of cyclohexyl p-aminobenzoate dissolved in 8.5 ml of ethanol was mixed, and after adding 1.4 ml of acetic acid to the mixture, the whole mixture was heated under a reflux condenser to bring the raw materials into condensation. After drying the reaction mixture to solid, and dissolving the solid into a solvent mixture of methanol and water, the solution was poured into an excess acetone. After collecting the thus separated precipitate by filtration, the precipitate was dissolved into methanol and the solution was subjected to the thin layer chromatography as in Example 9 to obtain a yellow powdery substance in a yield of 11%.

EXAMPLE 21

Synthesis of hexahydrobenzyl o-aminobenzoate-N-lactoside:

An aqueous solution of 3.6 g of lactose dissolved in 12 ml of water and a solution of 2.3 g of hexahydrobenzyl o-aminobenzoate dissolved in 4 ml of methanol were mixed, and after adding 1.4 ml of acetic acid to the mixture, the whole mixture was heated under a reflux condenser to bring the raw materials into condensation. During the reaction, since the reaction mixture separated into 2 phases, a small amount of dioxane was added to prevent the separation. After condensing the reaction mixture to dryness, the dried material was extracted with water and a large amount of chloroform. After drying the chloroform layer to solid and extracting the solid with water and ethyl ether, the aqueous layer was extracted with ethyl acetate and the extract was condensed to dryness to obtain a yellowish brown powdery substance in a yield of 1.4%.

EXAMPLE 22

Synthesis of hexahydrobenzyl m-aminobenzoate-N-L-fucoside:

In 20 ml of an aqueous 94% ethanolic solution, 2.1 g of hexahydrobenzyl m-aminobenzoate, 1.5 g of L-fucose and 0.2 g of ammonium chloride were heated under a reflux condenser to bring the raw materials into condensation. The reaction mixture was then condensed to dryness. The dried matter was subjected to the same procedures including the thin layer chromatography as in Example 10 to obtain a pale yellow powdery substance in a yield of 24.5%.

EXAMPLE 23

Synthesis of hexahydrobenzyl p-aminobenzoate-N-D-riboside:

In 25 ml of an aqueous 94% ethanolic solution, 3.5 g of hexahydrobenzyl p-aminobenzoate, 2.3 g of D-ribose and 0.2 g of ammonium chloride were heated under a reflux condenser to bring the raw materials into condensation. After condensing the reaction mixture to dryness, the dried material was subjected to the same procedures in Example 22 to obtain a pale yellow powdery substance in a yield of 5.4%.

EXAMPLE 24

Synthesis of hexahydrobenzyl p-aminobenzoate-N-D-glucoside:

The same condensation was carried out as in Example 23 except for using 2.7 g of D-glucose in 30 ml of 94% ethanolic solution instead of 2.3 g of D-ribose in 25 ml of 94% ethanolic solution in Example 23. The reaction mixture was evaporated to dryness and the dried material was dissolved in aqueous methanolic solution. After pouring the methanolic solution into an excess acetone and removing the thus separated precipitate by filtration, the filtrate was evaporated to dryness. The dried material was dissolved in methanol. The solution was subjected to the thin layer chromatography as in Example 9 to obtain a pale yellow powdery substance in a yield of 11.5%.

EXAMPLE 25

Synthesis of hexahydrobenzyl p-aminobenzoate-N-L-rhamnoside:

The same condensation was carried out as in Example 24 except for using 2.7 g of L-rhamnose in 25 ml of the 94% ethanolic solution instead of 2.7 g of D-glucose in 30 ml of the ethanolic solution in Example 24. After condensing the reaction mixture, and cooling the condensate, the thus separated crystals were recrystallized from the 94% ethanolic solution repeatedly to obtain colourless and needle-like crystals in a yield of 82%.

EXAMPLE 26

Synthesis of methyl p-aminophenylacetate-N-L-rhamnoside:

The same condensation was carried out as in Example 25 except for using 2.5 g of methyl p-aminophenylacetate instead of 3.5 g of hexahydro p-aminobenzoate in Example 25. After condensing the reaction mixture and pouring the condensate into an excess acetone, the thus separated precipitate was removed by filtration, and the filtrate was evaporated to be a syrupy material. After washing the syrupy material repeatedly with benzene, the washed material was dissolved in 20 ml of ethanol. By adding 5 ml of hexane to the ethanolic solution, crystalline substance was isolated and dired to be the product in a yield of 45%.

EXAMPLE 27

Synthesis of p-aminophenylacetic acid-N-L-rhamnoside:

Into ethanol, 1.51 g of p-aminophenylacetic acid and 1.82 g of L-rhamnose monohydrate were dissolved, and after adding 54 mg of ammonium chloride into the solution, the mixture was heated for 10 min under a reflux condenser in a stream of gaseous nitrogen. After filtering the reaction mixture by a sheet of filter paper, the filtrate was cooled. Then, the deposited crystals were collected by filtration and dried. The yield was 1.67 g. Purified p-aminophenylacetic acid-N-L-rhamnoside was obtained by recrystallizing the dried crystals with ethanol.

EXAMPLE 28

Synthesis of sodium p-aminophenylacetate-N-L-rhamnoside:

Into 3 ml of water containing 40 mg of sodium hydroxide, 297.30 mg of p-aminophenylacetic acid-N-L-rhamnoside obtained in Example 27 was dissolved. After condensing the solution and dissolving the condensate into 1 ml of methanol, the mixture was dispersed into a large amount of acetone. Then, the deposited crystals were collected by filtration and dried to obtain 150 mg of sodium p-aminophenylacetate-N-L-rhamnoside. Purification of the product was carried out by dissolving the crystals into methanol and dispersing the solution into a large amount of acetone.

EXAMPLE 29

Synthesis of potassium p-aminophenylacetate-N-L-rhamnoside:

Into 3 ml of water containing 56 mg of potassium hydroxide, 297.30 mg of p-aminophenylacetic acid-N-L-rhamnoside obtained in Example 27 was dissolved. After condensing the solution and dissolving the condensate into 1 ml of methanol, the mixture was dispersed into a large amount of acetone. Then, the deposited crystals were collected by filtration and dried to obtain 130 mg of potassium p-aminophenylacetate-N-L-rhamnoside. Purification of the crystals was carried out in the same manner as in Example 28.

FORMULATION EXAMPLE 1

One of the present substances, i.e., benzyl p-aminobenzoate-N-D-deoxyriboside (substance No. 13), heavy magnesium oxide and lactose were well mixed to be uniform powdery material or uniform minute particles at a weight ratio of 10:15:75 and the composition was sifted to collect the fraction smaller than 350μ in size to be a powdery composition. A capsuled composition was separately prepared by encapsulating this powdery composition.

FORMULATION EXAMPLE 2

One of the present substances, i.e., p-aminobenzoic acid amide-N-D-mannoside (substance No. 4), starch, lactose, crystalline cellulose, polyvinyl alcohol and water were uniformly mixed at a weight ratio of 45:15:16:21:3:30, and after crushing, granulating and drying the mixture to be granules, the product was sifted to collect the fraction of 177 to 1410μ in size. The thus obtained product was a granular composition.

FORMULATION EXAMPLE 3

Granular composition was prepared in the same manner as in Formulation Example 2 except for using phenyl o-aminobenzoate-N-L-rhamnoside (substance No. 6) instead of p-aminobenzoic acid amide-N-D-mannoside. Tablet-type composition was prepared separately by adding calcium stearate at a ratio of 4:96 to the granule and compressing the mixture into tablets of 10 mm in diameter.

FORMULATION EXAMPLE 4

Into 90 parts by weight of granules prepared in formalation Example 2, 10 parts by weight of crystalline cellulose, and 3 parts by weight of calcium stearate were added, and after compressing the mixture to be tablets of 8 mm in diameter, a mixed suspension of syrup, gelatin and precipitated calcium carbonate was added to the tablets to prepare sugar-coated tablets.

FORMULATION EXAMPLE 5

A mixture of 0.6 part by weight of m-aminobenzoic acid amide-N-cellobioside (Substance No. 2), 2.4 parts by weight of a non-ionic surfactant and 97 parts by weight of an aqueous physiological saline solution was prepared while warming the components. The mixture was dividedly introduced into ampules and sterilized to be injection.

What is claimed is:

1. Derivatives of a saccharide, represented by the general formula (I)

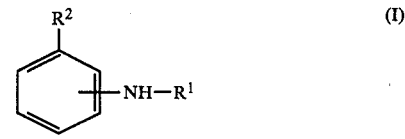

wherein $R^1$ represents a residual group formed by removing one hydroxyl group from the reducing end of a monosaccharide, disaccharide or trisaccharide; $R^2$ represents

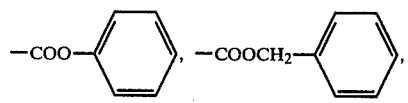

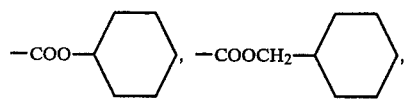

—CONH$_2$ or —CH$_2$COOR$^3$ and R$^3$ represents a hydrogen atom, an alkyl of one to four carbon atoms or an equivalent of pharmaceutically acceptable metal.

2. Derivatives of a saccharide according to claim 1, wherein said residual group is one member selected from the group consisting of the residual groups formed by removing one hydroxyl group at position 1 (alpha) or position 1 (beta) of ribose, deoxyribose, glucose, fructose, xylose, mannose, rhamnose, fucose, lactose, cellobiose and maltotriose.

3. Derivatives of a saccharide according to claim 1, wherein R$^1$ of the general formula (I) represents —CH$_2$COOR$^3$ and R$^3$ is a hydrogen atom.

4. Derivatives of a saccharide according to claim 1, wherein R$^1$ of the general formula (I) represents —CH$_2$COOR$^3$ and R$^3$ is Na, K, $\frac{1}{2}$Ca, $\frac{1}{2}$Mg or $\frac{1}{3}$Al.

5. Derivatives of a saccharide according to claim 1, wherein R$^1$ of the general formula (I) represents —CH$_2$COOR$^3$ and R$^3$ is a methyl-, ethyl-, propyl- or butyl group.

6. o-Aminobenzoic acid amide-N-D-fructoside.
7. m-Aminobenzoic acid amide-N-cellobioside.
8. p-Aminobenzoic acid amide-N-D-xyloside.
9. p-Aminobenzoic acid amide-N-D-mannoside.
10. p-Aminobenzoic acid amide-N-L-rhamnoside.
11. Phenyl o-aminobenzoate-N-L-rhamnoside.
12. Phenyl m-aminobenzoate-N-D-mannoside.
13. Phenyl p-aminobenzoate-N-D-xyloside.
14. Phenyl p-aminobenzoate-N-cellobioside.
15. Phenyl p-aminobenzoate-N-maltotrioside.
16. Benzyl m-aminobenzoate-N-L-fucoside.
17. Benzyl m-aminobenzoate-N-lactoside.
18. Benzyl p-aminobenzoate-N-D-deoxyriboside.
19. Benzyl p-aminobenzoate-N-D-glucoside.
20. Benzyl p-aminobenzoate-N-D-fructoside.
21. Cyclohexyl o-aminobenzoate-N-D-deoxyriboside.
22. Cyclohexyl m-aminobenzoate-N-D-mannoside.
23. Cyclohexyl p-aminobenzoate-N-D-xyloside.
24. Cyclohexyl p-aminobenzoate-N-cellobioside.
25. Cyclohexyl p-aminobenzoate-N-maltotrioside.
26. Hexahydrobenzyl m-aminobenzoate-N-lactoside.
27. Hexahydrobenzyl m-aminobenzoate-N-L-fucoside.
28. Hexahydrobenzyl p-aminobenzoate-N-D-riboside.
29. Hexahydrobenzyl p-aminobenzoate-N-D-glucoside.
30. Hexahydrobenzyl p-aminobenzoate-N-L-rhamnoside.
31. Methyl p-aminophenylacetate-N-L-rhamnoside.
32. p-Aminophenylacetic acid-N-L-rhamnoside.
33. Sodium p-aminophenylacetate-N-L-rhamnoside.
34. Potassium p-aminophenylacetate-N-L-rhamnoside.

35. A pharmaceutical composition in a dosage unit form, which comprises a derivative of a saccharide represented by the general formula:

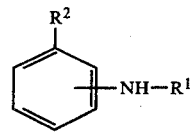

wherein R$^1$ represents a residual group formed by removing one hydroxyl group from the reducing end of a monosaccharide, disaccharide or trisaccharide; R$^2$ represents

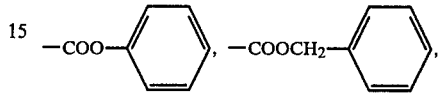

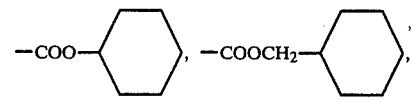

—CONH$_2$ or —CH$_2$COOR$^3$, and R$^3$ represents a hydrogen atom, an alkyl group of one to four carbon atoms or an equivalent of pharmaceutically acceptable metal, and a pharmaceutically acceptable carrier or diluent.

36. A method for the treatment of hydperglycemia, hyperlipemia, inflammatory diseases, pains due to the accentuation of central nerve, pyrexia due to the accentuation of central nerve and tumor, which comprises administering to a mammal suffering from hyperglycemia, hyperlipemia, inflammatory diseases, pains due to the accentuation of central nerve, pyrexia due to the accentuation of central nerve and tumor an effective amount of a compound of the formula (I):

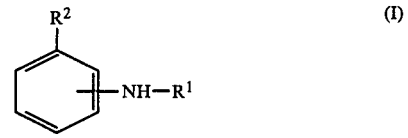 (I)

wherein R$^1$ represents a residual group formed by removing one hydroxyl group from the reducing end of a monosaccharide, disaccharide or trisaccharide; R$^2$ represents

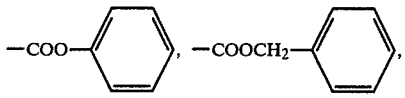

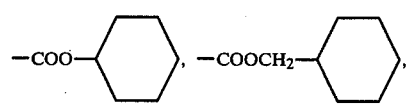

—CONH$_2$ or —CH$_2$COOR$^3$ and R$^3$ represents a hydrogen atom, an alkyl of one to four carbon atoms or an equivalent of pharmaceutically acceptable metal.

* * * * *

UNITED STATES PATENT AND TRADEMARK OFFICE
CERTIFICATE OF CORRECTION

PATENT NO. : 4,372,948

DATED : February 8, 1983

INVENTOR(S) : Chikao YOSHIKUMI ET AL

It is certified that error appears in the above-identified patent and that said Letters Patent is hereby corrected as shown below:

Claim 3, line 2, change "$R^1$" to --$R^2$--.

Claim 4, line 2, change "$R^1$" to --$R^2$--.

Claim 5, line 2, change "$R^1$" to --$R^2$--.

Signed and Sealed this

Thirtieth Day of August 1983

[SEAL]

Attest:

Attesting Officer

GERALD J. MOSSINGHOFF

Commissioner of Patents and Trademarks